(12) United States Patent
Yagi et al.

(10) Patent No.: US 9,724,164 B2
(45) Date of Patent: Aug. 8, 2017

(54) BLOOD-VESSEL BLOODSTREAM SIMULATION SYSTEM, METHOD THEREFOR, AND COMPUTER SOFTWARE PROGRAM

(75) Inventors: Takanobu Yagi, Tokyo (JP); Young-Kwang Park, Tokyo (JP)

(73) Assignee: EBM CORPORATION, Tokyo (JP)

( * ) Notice: Subject to any disclaimer, the term of this patent is extended or adjusted under 35 U.S.C. 154(b) by 755 days.

(21) Appl. No.: 14/240,707

(22) PCT Filed: Aug. 27, 2012

(86) PCT No.: PCT/JP2012/071626
§ 371 (c)(1),
(2), (4) Date: Jul. 7, 2014

(87) PCT Pub. No.: WO2013/031743
PCT Pub. Date: Mar. 7, 2013

(65) Prior Publication Data
US 2014/0343906 A1    Nov. 20, 2014

(30) Foreign Application Priority Data
Aug. 26, 2011   (JP) ................................. 2011-184751

(51) Int. Cl.
*G06F 17/50*    (2006.01)
*A61B 19/00*    (2006.01)
(Continued)

(52) U.S. Cl.
CPC .............. *A61B 19/50* (2013.01); *A61B 5/026* (2013.01); *A61B 5/055* (2013.01); *A61B 5/7275* (2013.01);
(Continued)

(58) Field of Classification Search
USPC .................................................... 703/2, 5, 7
See application file for complete search history.

(56) References Cited

U.S. PATENT DOCUMENTS

| 7,840,393 B1 | 11/2010 | Whirley et al. |
| 2005/0018885 A1 | 1/2005 | Chen et al. |

(Continued)

FOREIGN PATENT DOCUMENTS

| JP | 2002-513601 A | 5/2002 |
| JP | 2004-528858 A | 9/2004 |

(Continued)

OTHER PUBLICATIONS

Supplementary Partial European Search Report (EP12827397).
(Continued)

*Primary Examiner* — Thai Phan
(74) *Attorney, Agent, or Firm* — Konomi Takeshita

(57) ABSTRACT

This system is a system for analyzing blood flow which imposes a boundary condition relating to the blood flow to three dimensional shape data of a target vascular site of a subject and divides a lumen of the target vascular site into meshes for obtaining state quantities of the blood flow at each mesh position by means of computation, having: a labeling unit, by a computer, for reading out the three dimensional shape data on the lumen of the target vascular site, and labeling a plurality of vascular elements included in the target vascular based on a size of the cross-sectional area of each of the vascular elements; wherein, the computation of the state quantities is carried out by varying a level of mesh detail for each vascular element based on the labeling according to the size of the cross-sectional area.

32 Claims, 27 Drawing Sheets

(51) Int. Cl.

| | | |
|---|---|---|
| A61B 5/055 | (2006.01) | |
| A61B 5/026 | (2006.01) | |
| G06T 19/00 | (2011.01) | |
| G06T 17/00 | (2006.01) | |
| A61B 5/00 | (2006.01) | |
| A61B 17/08 | (2006.01) | |
| A61B 17/12 | (2006.01) | |
| A61F 2/82 | (2013.01) | |
| A61F 2/95 | (2013.01) | |
| A61B 34/00 | (2016.01) | |
| A61B 90/00 | (2016.01) | |
| A61B 6/00 | (2006.01) | |
| A61B 8/06 | (2006.01) | |
| A61B 5/02 | (2006.01) | |
| G06F 19/00 | (2011.01) | |
| A61B 34/10 | (2016.01) | |

(52) U.S. Cl.
CPC ............ *A61B 6/507* (2013.01); *A61B 17/083* (2013.01); *A61B 17/12118* (2013.01); *A61B 34/10* (2016.02); *A61B 34/25* (2016.02); *A61B 90/37* (2016.02); *A61F 2/82* (2013.01); *A61F 2/95* (2013.01); *G06F 17/5009* (2013.01); *G06F 19/3437* (2013.01); *G06T 17/00* (2013.01); *G06T 19/00* (2013.01); *A61B 5/02014* (2013.01); *A61B 5/7435* (2013.01); *A61B 6/504* (2013.01); *A61B 8/06* (2013.01); *A61B 2034/104* (2016.02); *A61B 2034/105* (2016.02); *A61B 2034/107* (2016.02); *A61B 2034/108* (2016.02); *A61B 2576/02* (2013.01); *G06F 19/321* (2013.01); *G06T 2210/24* (2013.01); *G06T 2210/41* (2013.01)

(56) References Cited

U.S. PATENT DOCUMENTS

| | | |
|---|---|---|
| 2008/0044072 A1 | 2/2008 | Kiraly et al. |
| 2008/0228086 A1 | 9/2008 | Ilegbusi et al. |
| 2010/0114302 A1* | 5/2010 | Tzafriri ............... A61F 2/06 623/1.42 |
| 2010/0128963 A1 | 5/2010 | Waku et al. |
| 2010/0260400 A1 | 10/2010 | Bernhardt et al. |
| 2011/0093243 A1 | 4/2011 | Tawhai et al. |
| 2014/0316785 A1* | 10/2014 | Bennett ............... G06F 17/3043 704/254 |
| 2015/0127031 A1* | 5/2015 | Yagi ................... A61B 5/055 606/158 |
| 2015/0127085 A1* | 5/2015 | Tzafriri ............... A61F 2/06 623/1.13 |

FOREIGN PATENT DOCUMENTS

| | | |
|---|---|---|
| JP | 2010-148866 A | 7/2010 |
| JP | 2010-207531 A | 9/2010 |
| JP | 2011-040055 A | 2/2011 |

OTHER PUBLICATIONS

A.-V. Salsac, Evolution of the wall shear stresses during the progressive enlargement of symmetric abdominal aortic aneurysms, J. Fluid Mech., 2006, vol. 560, p. 19-51.

A. Mantha, Hemodynamics in a Cerebral Artery before and after the Formation of an Aneurysm, American Journal of Neuroradiology, 2006, vol. 27, p. 1113-1118.

* cited by examiner

Ophthalmic artery
(Diameter 1 mm)

Internal carotid artery
(Diameter 5mm)

Wall Shear Stress and Pressure

Wall Shear Stress

Wall Shear Stress Vector

Pressure

Flow Disturbance Index (Divergent)

BLOOD-VESSEL BLOODSTREAM SIMULATION SYSTEM, METHOD THEREFOR, AND COMPUTER SOFTWARE PROGRAM

CROSS REFERENCE TO RELATED APPLICATIONS

This application is a United States national phase of co-pending international patent application No. PCT/JP2012/071626, filed Aug. 27, 2012, which claims benefit of Japanese Patent Application No. 2011-184751, filed Aug. 26, 2011, the disclosures of which are incorporated herein by reference.

FIELD OF THE INVENTION

The present invention relates to a system for simulating blood flow, method thereof, and computer software program.

BACKGROUND OF THE INVENTION

Cardiovascular diseases appear in various types of lesions including aneurysm, atherosclerosis, and stenosis. These diseases are caused by pathological changes of normal parts with an influence of blood flow, and although the diseases would be fatal in many cases depending on their growth stages, it is extremely difficult to treat them because such a treatment may risk the patient's life span. For understanding these refractory cardiovascular diseases, it is beneficial to apply advanced engineering technology including fluid analysis and structural analysis, in addition to the fundamental medical approach of studying underlying pathology.

For example, cerebral aneurysm is an angiopathy where a part of a cerebral artery wall protrudes outward, forming a shape similar to a balloon, and there are an increasing number of clinical cases of accidentally discovering an un-ruptured aneurysm while conducting a brain image diagnosis. A cerebral aneurysm appears due to the vulnerability of the cerebral artery wall, altering a part of the wall to develop a lump which is fragile due to the lack of the tunica media, and it is most likely a cause of subarachnoid hemorrhage because many cases of cerebral aneurysm tend to appear in the subarachnoid space. Therefore, a cerebral aneurysm giving a high potential of rupture needs to be treated proactively by conducting a proper surgical treatment such as a stent treatment.

However, the probability of the actual rupture of cerebral aneurysms is reported to be less than 1% annually for the size 10 mm or less; thus, considering the risk of post-surgical complication, preventive treatment would not be necessarily appropriate in some cases, and consequently rather than relying on surgical treatment alone, it is required to determine a subject to be treated by judging an aneurysm at a greater probability of rupture. For this reason, there have been research conducted on methods for diagnosing a cerebral aneurysm based on its size and shape, the family record, the blood pressure, and the habit of cigarette smoking, and other factors of the patient. Nevertheless, these indicators are not deterministic factors of the diagnosis, and developing a more effective diagnostic method is demanded.

Japanese Patent Application Publication No. 2010-207531 discloses MRI equipment that may diagnose the risk of aneurysmal rupture by analyzing the viscous force of fluid that exerts on the inner wall of cerebral aneurysm, i.e., by analyzing the magnitude of wall shear stress of the fluid.

However, regarding the correlation between the magnitude of the wall shear stress and the growth of aneurysm there are several controversial arguments where the diagnostic results are contradicting each other. A first theory is the High Wall Shear Stress (WSS) theory which explains that cerebral aneurysm grows due to an appearance of an endothelial cell fault once the wall shear stress exceeds a certain threshold value which results in the infiltration of migratory cells, leading to reduce the mechanical strength of the aneurysm wall. A second theory is the Low WSS theory which explains that once the wall shear stress drops below a certain threshold value, platelets or white blood cells that adhere to the endothelial cells lower the endothelial function, resulting in the reduction of the mechanical strength of the aneurysm wall. Because those theories have explanations opposite to each other, the magnitude of the wall shear stress is not a direct measure of determining the growth and rupture of the aneurysm.

There are other attempts to determine the rupturing risk by investigating the magnitude of the wall shear stress, e.g., a method for analyzing the blood flow either experimentally or computationally to extract the wall shear stress from medical images acquired by MRI or CT. However, as pointed out above, there is no conclusive correlation between the magnitude of the wall shear stress and the risk of rupture, and furthermore, the method of using medical images medical image is a methodology that is only based on the morphology of a vascular lumen, and thus provides no interpretation of the flow itself. This is because the observation of medical images fails to allow us to obtain pathological information of cellular conditions and morphological information of aneurysmal wall thickness, which change locally on the aneurysm wall, while the magnitude of the wall shear stress itself also varies locally on the aneurysm wall.

Considering the above issues, the present invention has been researched and developed, aiming the purpose that provides a method for determining a possible appearance of lesion in a target vascular site and its potential growth based upon a diagnostic result of the blood flow characteristics of the targeted blood vessel, and furthermore, and predicting the effect of treatment, a system thereof, and an accompanied software program.

SUMMARY OF THE INVENTION

In order to solve the above mentioned problem, according to the first main aspect of the present invention, there is provided a system for analyzing blood flow which imposes a boundary condition relating to the blood flow to three dimensional data representing a shape of a target vascular site of a subject and divides a lumen of the target vascular site into meshes for obtaining state quantities of the blood flow at each mesh position by means of computation, comprising:

a labeling unit, by a computer, for reading out the three dimensional data on the lumen of the target vascular site, and labeling a plurality of vascular elements included in the target vascular based on a size of a cross-sectional area of each of the vascular elements; wherein, the computation of the state quantities is carried out by varying a level of mesh detail for each vascular element based on the labeling according to the size of the cross-sectional area.

According to an embodiment of the present invention, the labeling unit has a storage unit, by a computer, for storing names of principal and other vascular elements contained in a specific target vascular site in conjunction with the specific target vascular site, and; a unit, by a computer, for measuring cross-sectional area of each of vascular elements contained in a specific target vascular site in a plurality of cross sections, identifying a blood vessel with a largest median value of the area as a principal blood vessel as well as other vascular elements based on the determination of the principal blood vessel, labeling the names of the principal and other vascular elements, and then outputting the labels together with the three-dimensional data.

In this case, the level of mesh detail is determined by a magnitude of a median value of the cross-sectional area from a plurality of levels that range from coarse to fine.

According another embodiment, the system further comprises a computational condition storage unit, by a computer, for storing multiple sets of computational conditions including boundary conditions to calculate state quantities of blood flow that flows through the three-dimensional data, wherein the multiple sets of the computational conditions contain one or more different computational condition values for a calculation speed that a user requires, wherein the system provides a user with a list of possible computational speed, reads out a set of computational condition values relating to the selected computational speed, calculates the blood flow state quantities based on the computational condition values included in the selected set, and outputs calculated results.

In this case, at least one set of the multiple sets of computational condition values preferably contains a computational condition value which assumes a steady blood flow when a user requires a fast calculation speed, and at least another set of the multiple sets of the computational condition values contains a computational condition value which assumes a pulsatile blood flow when a user requires better calculation accuracy rather than calculation speed.

In addition, in this case, at least another set of computational condition values preferably contain a computational condition value under consideration of transition from a laminar flow to a turbulent flow within a pulsation cycle of the pulsatile blood flow.

Furthermore, this system preferably further has a first processor for carrying out calculations for which a user requires more computational speed; a second processor for carrying out calculations for which a user requires more computational accuracy; and a processor determination unit for determining which processor to be used according to a choice made by a user. In this case, it is desirable that the second processor conducts parallel analyses by employing a plurality of high speed arithmetic operation units. Furthermore, the second processor is preferably installed in a separate location which is connectable with the system through a communication network, and, when the processor determination unit determines that the second processor is to be used, the processor determination unit sends a part or all of the conditions required for computation to the second processor and receives calculation results via the communication network.

According to yet another embodiment of the present invention, this system further comprises a surgical simulation unit, by a computer, for generating three-dimensional data representing a shape of the target vascular site after a surgery by means of a simulation; wherein the surgical simulation unit comprises: a treatment method receiving unit, by a computer, for displaying the three-dimensional data on a computer display screen, and receiving a specification of a lesion on display and a selection of a surgical treatment method for the lesion; a modification method storage unit, by a computer, for pre-storing selectable treatment methods and methods for modifying the three-dimensional data for respective treatment methods; and a modified three-dimensional shape data output unit, by a computer, for reading out a modification method from the modification method storage unit according to the selection of a treatment method, modifying the three-dimensional shape data related to the specification of the lesion by the selected method, and outputting the modified three-dimensional shape data.

In this case, the selectable treatment methods preferably include coil embolization; wherein a method for modifying the three-dimensional data for the coil embolization comprises a unit for placing a porous structure on a part of the lumen of the target vascular site on the three-dimensional data in order to simulate a state of blocking the part of the lumen of the target vascular site with the coil embolization. In addition, the system preferably further comprises a unit for adjusting a coil filling ratio with an aperture ratio of the porous structure.

In another example, the selectable treatment methods preferably include clipping, wherein a method for modifying the three-dimensional data for the clipping method comprises a unit for removing one or more polygons which configure a surface of a part of the vascular lumen (i.e., a part that forms a lump), and a unit for regenerating the removed surface with one or more different polygons in order to simulate a state of completely blocking the part of the vascular lumen.

Furthermore, the selectable treatment methods preferably include stent implantation, wherein the method for modifying the three-dimensional data appropriate to this treatment method comprises a unit for modifying an uneven surface on a part of the vascular lumen by moving or distorting polygons in order to conduct a simulation of controlling blood flow in a blood vessel by applying a stent.

In addition, the selectable treatment methods preferably include flow-diverting stent implantation, wherein the method for modifying the three-dimensional data appropriate to this treatment method comprises a unit for defining a lattice structured object on the lumen of the target vascular site on the three-dimensional data in order to conduct a simulation of restricting blood flow by implanting a flow-diverting stent. In this case, the system preferably has a unit for adjusting a pore density with an aperture ratio of the lattice structured object.

According to still another embodiment of the present invention, this system further comprises a shape modification unit for modifying the three dimensional data; wherein the shape modification unit comprises a modification site specification unit, by a computer, for displaying the three-dimensional data on a computer display screen, and receiving a specification of at least one polygon of a part of the three-dimensional data for which unevenness thereof is to be modified on the display; a polygon shifting unit, by a computer, for moving or distorting the at least one polygon, with its center of gravity as a starting point, outward or inward of the blood vessel along a direction normal to the vascular wall surface, and a smoothing unit, by a computer, for detecting an acute angle part in the at least one polygon that is moved or distorted by the polygon shifting unit, and smoothing out the acute angle part.

In this case, it is preferable that the system further comprises a blood flow characteristic determination unit for determining, from the state quantities of the blood flow obtained by the computation at each mesh position, a wall shear stress vector at each position of the wall surface of the target vascular site, determining relative relationship between a direction of the wall shear stress vector at a specific wall surface position and directions of wall shear stress vectors at wall surface positions surrounding the specific wall surface position, and from a morphology thereof, determining characteristics of the blood flow at the specific wall surface position, and outputting the same as a determined result; and a display unit, by a computer, for displaying the determined result of the blood flow characteristic which is graphically superposed onto a three-dimensional shape model.

Furthermore, it is preferable that the blood flow characteristics determination unit determines whether the relative relationship between the direction of the wall shear stress vector at the specific position of the wall surface and the directions of the wall shear stress vectors at positions on the wall surface surrounding the specific position is "parallel", "confluent", "rotational", or "divergent", and determines the blood flow characteristics to be benign (or non-malignant) if the relative relationship is "parallel", otherwise malignant (or non-benign).

In addition, it is desirable that if the blood flow characteristics determination unit determines that the relative relationship between the direction of the wall shear stress vector at the specific position of the wall surface and the directions of the wall shear stress vectors at positions of the wall surface surrounding the specific position is "divergent", the determination unit determines that thinning of the vascular wall at the specific position may occur, and the display unit outputs the position of potential wall-thinning, superposed onto the three-dimensional shape model graphically.

Furthermore, the blood flow characteristic determination unit preferably computes a rotation: rot $\tau$, and a divergence: div $\tau$, which are scalar quantities of a wall shear stress vector field: $\tau$, from a relative angular relationship between the wall shear stress vector $\tau$ at the specific position of the wall surface and a plurality of wall shear stress vectors at positions of the wall surface surrounding the specific position, defines these values as a flow disturbance index, and compares them with threshold values to determines the flow disturbance index to be "parallel", "confluent", "rotational", or "divergent";

wherein if the value of rot $\tau$ of the flow disturbance index is either a negative or positive value outside a predetermined threshold range, it is determined as "rotational";

if the value of div $\tau$ of the flow disturbance index is a negative value outside a predetermined threshold range, it is determined as "confluent";

if the value of div $\tau$ of the flow disturbance index is a positive value outside a predetermined threshold range, it is determined as "divergent"; and if the values of rot $\tau$ and div $\tau$ of the flow disturbance index are both in a predetermined threshold range, it is determined as "parallel". In this case, it is desirable that the blood flow characteristics determination unit preferably regards the plurality of the wall shear stress vectors as unit vectors for mathematical operations, and the threshold value to be compared with the rot $\tau$ and the div $\tau$ is zero.

In addition, the blood flow characteristics determination unit preferably obtains the numerical values of the rot $\tau$ and div $\tau$ of the flow disturbance index by giving, as a weight coefficient, an index value of a pressure that acts in a direction normal to the specific wall surface position, to the rot $\tau$ and the div $\tau$ values.

Furthermore, it is desirable that the index value of the pressure that is provided when calculating the values of the rot $\tau$ and the div $\tau$ of the flow disturbance index is a value obtained by dividing the pressure at the specific position of the wall surface by a mean value of pressure on the wall surface of the target vascular site.

In addition, the display unit preferably displays the numerical values of the rot $\tau$ and/or the div $\tau$ of the flow disturbance index with the three-dimensional shape model on which they are superposed.

According to yet another embodiment of the present invention, the blood flow characteristic determination unit computes a rotation rot $\tau$ and a divergence div $\tau$ of a wall shear stress vector field $\tau$ from a relative relationship between a wall shear stress vector $\tau$ at a specific position of the wall surface and a plurality of wall shear stress vectors at positions of the wall surface surrounding the specific position, compares these values as a flow disturbance index with threshold values, and determines that the blood flow characteristics is benign (or non-malignant) if the calculated values are within a threshold range; and the blood flow characteristics is malignant (or non-benign) if the calculated values are outside the threshold range.

The second main aspect of the present invention provides a computer software program for operating the systems of the present invention.

The third main aspect of the present invention provides a method for operating the systems of the present invention.

The characteristics of the present invention which are not described above are disclosed in the disclosure of embodiments of the present invention, and accompanied figures shown hereinafter in details so that those skilled in the art may work out the present invention.

DETAILED DESCRIPTION OF THE INVENTION

Figure 1:
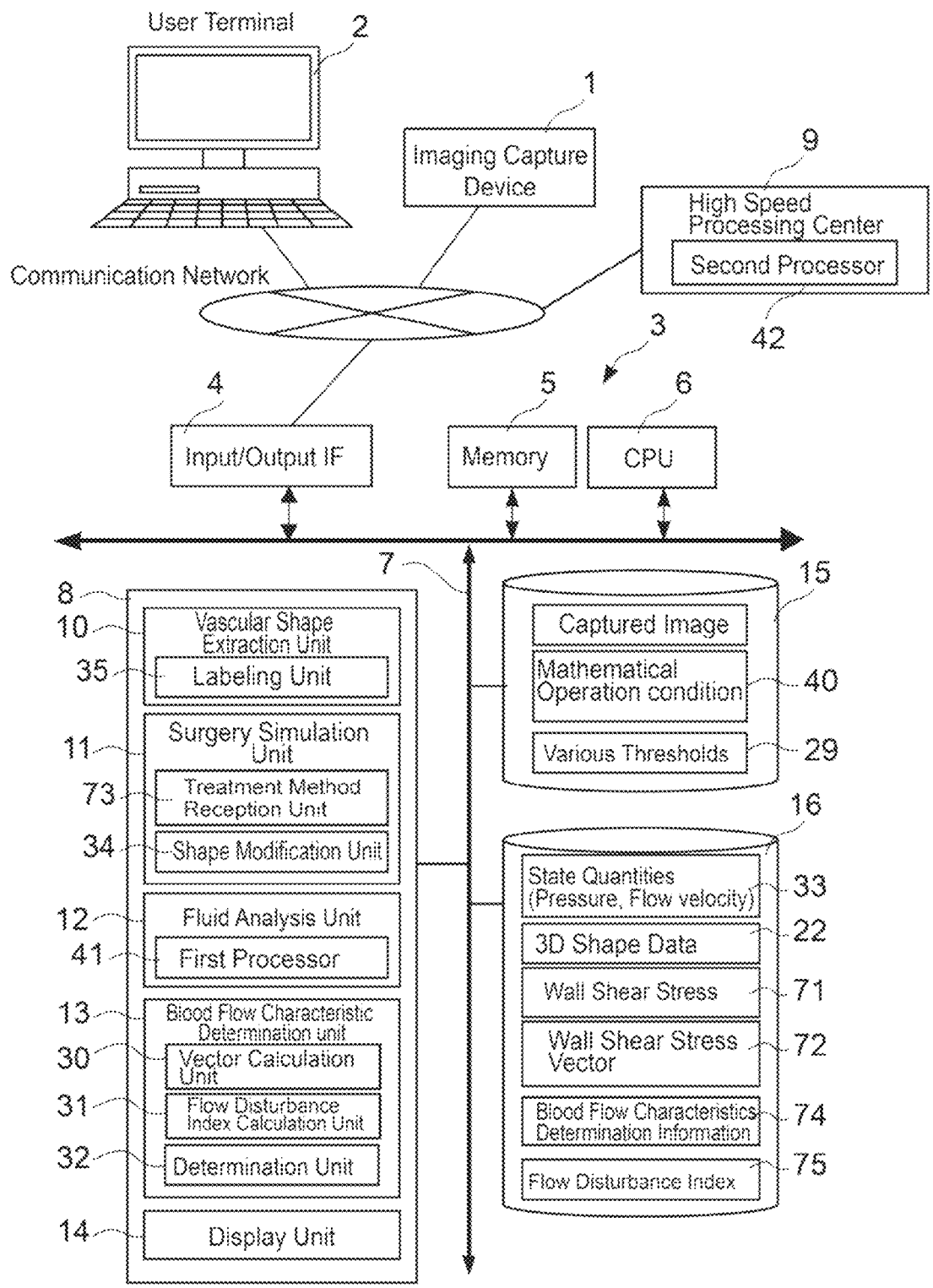
FIG. 1 shows a schematic diagram of an embodiment of the present invention.

Referring to figures herein, an embodiment of the present invention is now described in detail below. In the description hereinafter, a cerebral aneurysm is presented as a cardiovascular disease that may become a subject of diagnosis and treatment.

(System for Diagnosing Blood Flow Characteristics Based on Malignant/Benign Blood Flow Patterns)

As described above, the first main aspect of the present invention is to provide a diagnostic system for characterizing cerebral aneurysms. The present invention associates the morphology of shear stress vectors acting on the aneurysmal wall by blood flow, with the information on the luminal geometry, pathology, and wall thickness of aneurysm in order to categorize the vectors to either a "malignant blood flow pattern" which would become a potential risk of appearance of lesion or its growth or a "benign blood flow pattern" which would not become the potential risk. The morphology of the shear stress vectors produced by the simulation determines whether the vectors imply either a malignant blood flow pattern or a benign blood flow pattern. If it is a malignant blood flow pattern, it would be a potential risk of appearance or growth of a lesion, which may require considering a surgery whereas if it is a benign blood flow pattern, it would not be the potential risk, and may avoid a risk of unnecessary surgery.

(System for Predicting Treatment Effect of Blood Vessel)

The second aspect of the present invention is to provide a system, e.g., a system for predicting the treatment effect of a cerebral aneurysm, which is determined to have a malignant blood flow pattern.

In other words, a method for determining the blood flow characteristics to be malignant or benign may be applied not only for pre-treated aneurysms, but also post-treated aneurysms in terms of predicting the treatment effect.

The surgical treatment for a cerebral aneurysm includes: 1) clipping, 2) coil embolization, and 3) stent placement (flow-diverting stent).

The clipping method blocks the blood flow inside a cerebral aneurysm by closing a neck part of the aneurysm with a clip; i.e., it constructs a new vascular morphology that does not have the cerebral aneurysm. The coil embolization places a plural number of coils in an aneurysm to create thrombus in the lump for blocking the blood flow. The flow-diverting stent method places a mesh like object that is made of metal or other materials at the neck of an aneurysm to reduce the fluid flow through the lump and form a thrombus in it for blocking the flow.

Those treatment methods have a common feature of blocking the fluid flow in a cerebral aneurysm, and they reconstruct a new lump neck, i.e., a new vascular shape by altering the cerebral aneurysm artificially. A post-treatment complication may appear as the reconstructed vascular morphology gradually changes in the course of time. For example, in a case of the coil embolization treatment, the reconstructed lump neck may be compressed into the lumen by the fluid force, resulting in the reopening of a path between the main blood vessel and the lumen of lump, and thus a re-treatment is often required.

In such a case, first, the vascular morphology which is a three-dimensional model created by a computer is modified to create a new lump neck by a computer artificially so that a computer may construct a vascular morphology similar to one to be formed by conducting an actual surgery. Second, the morphology of the shear stress vectors acting on the wall of the newly created blood vessel is visualized by a simulation to apply the method for determining if the simulated blood flow pattern is malignant or benign so that the treatment effect by the surgery may be evaluated in advance. In other words, by applying the method for determining the malignant or the benign blood flow pattern, it is possible to predict a direction of progress of whether the vascular cells such as endothelial cells grow and adhere to the part of the blood vessel to reproduce the vascular tissue properly and regain the adequate mechanical strength, and those observations by simulation may contribute to the accurate prediction of the treatment effect to reduce a post-surgical complication and even death of a patient.

(Configuration of a System for Determining the Blood Flow Characteristics Diagnosis/Predicting the Treatment Effect Related to this Embodiment)

FIG. 1 shows a schematic diagram of a system for determining the blood flow characteristics/predicting the treatment effect related to this embodiment. The blood flow characteristics determination/treatment effect prediction system corresponds to the first and the second aspects of the present invention, which has the following two capabilities.

(1) For considering if the subjective cerebral aneurysm has a probability of an appearance of lesion or its potential growth, the system determines automatically whether the target vascular site of a subject is either a benign blood flow pattern that would not rupture the cerebral aneurysm or a malignant (non-benign) blood flow that would rupture the cerebral aneurysm.

(2) When the cerebral aneurysm is to be surgically treated, by conducting a surgical simulation in order to predict the post-surgical blood flow, the system determines automatically whether the blood flow pattern would be either a benign blood flow that would not develop a risk of post-surgical complication or death, or a malignant blood flow that would develop a risk of post-surgical complication or death.

In order to perform those functions, this system for diagnosing blood flow characteristics/predicting the treatment effect is installed at a site (e.g., a hospital) of a user such as a doctor as shown in FIG. 1, which equips with an image capture device 1 that takes images of cerebral aneurysm and surrounding target vascular sites, a user terminal 2 with which a user such as a doctor may operate the system, and a blood flow characteristics diagnostic/treatment effect prediction system server 3 which connects the image capture device 1 and the user terminal 2 through a communication network (an in-hospital LAN, an out-of-hospital WAN, or a designated communication line).

Here, the image capture device 1 may be an instrument that acquires a tomographic image of the target vascular site, by using a Computed Tomography (CT) scanner, an Magnetic Resonance Imaging (MRI) system, a Digital Subtraction Angiography (DSA) equipment, and other medical instruments that acquire images of the target vascular site by applying methods such as the ultrasound Doppler and the near infrared imaging technology.

The aforementioned user terminal 2 may be a workstation consisting of a standard personal computer that runs a display software program such as a browser capable of displaying a graphical interface for establishing communication with a server of the blood flow characteristics determination/treatment effect prediction system.

The server 3 of the blood flow characteristics determination/treatment effect prediction system consist of a program storage unit 8 connected with a bus line 7 that connects an input/output interface 4 used for establishing communication with the communication network, a memory 5, and a CPU 6. The program storage unit 8 is configured with a vascular shape extraction unit (i-Vessel) 10 that produces a set of three-dimensional data of a target vascular site by using the image data acquired by the image capture device 1, a surgical simulation unit (i-Surgery) 11 that runs a surgical simulation by manipulating the three-dimensional data, a fluid analysis unit (i-CFD) 12 that computes the state quantities of the blood flow at the target vascular site, a blood flow characteristics determination unit (i-Flow) 13 that determines the blood flow at the target vascular site whether it is benign or malignant, and a display unit 14 that has a user graphical interface produced by the system and a display screen to show the image, the analysis result and the determined outcome. There are two databases connected with the bus line 7: a simulation setting DB 15 that stores various setting information for conducting the simulation, and a simulation result DB 16 that stores outcomes of the simulation and the analysis.

The components of the server 3 (the vascular shape extraction unit 10, the surgical simulation unit 11, the fluid analysis unit 12, and the blood flow determination unit 13) are actually constructed by computer software programs that are stored in a memory area of a hard drive of a computer, and the CPU 6 deploys the software programs from the hard drive to the memory 5 for executing the programs so that the components of the present invention performs their functions. A single computer may configure the server 3, or multiple computers may configure a distributed server as the server 3 as well.

In the above example, the server 3 of the blood flow characteristics determination/treatment effect prediction system connects with a user terminal 2 in a hospital through a communication network, and the server may be installed in a hospital or in a high speed process center 9 outside a hospital. In the latter case, the server is preferably configured to receive data and instructions from a number of user terminals 2 and image capture devices 1 of several hospital sites, and executes highly accurate fluid analysis using a high speed processor, and then feeds back the analysis outcome to the user terminals in each hospital so that a user such as a doctor may display the analysis outcome on screen for a patient and other people on the spot.

Referring to actual system operations, the capability of this blood flow characteristics determination/treatment effect prediction system is disclosed hereinafter.

(User Graphical Interface)

Figure 2:
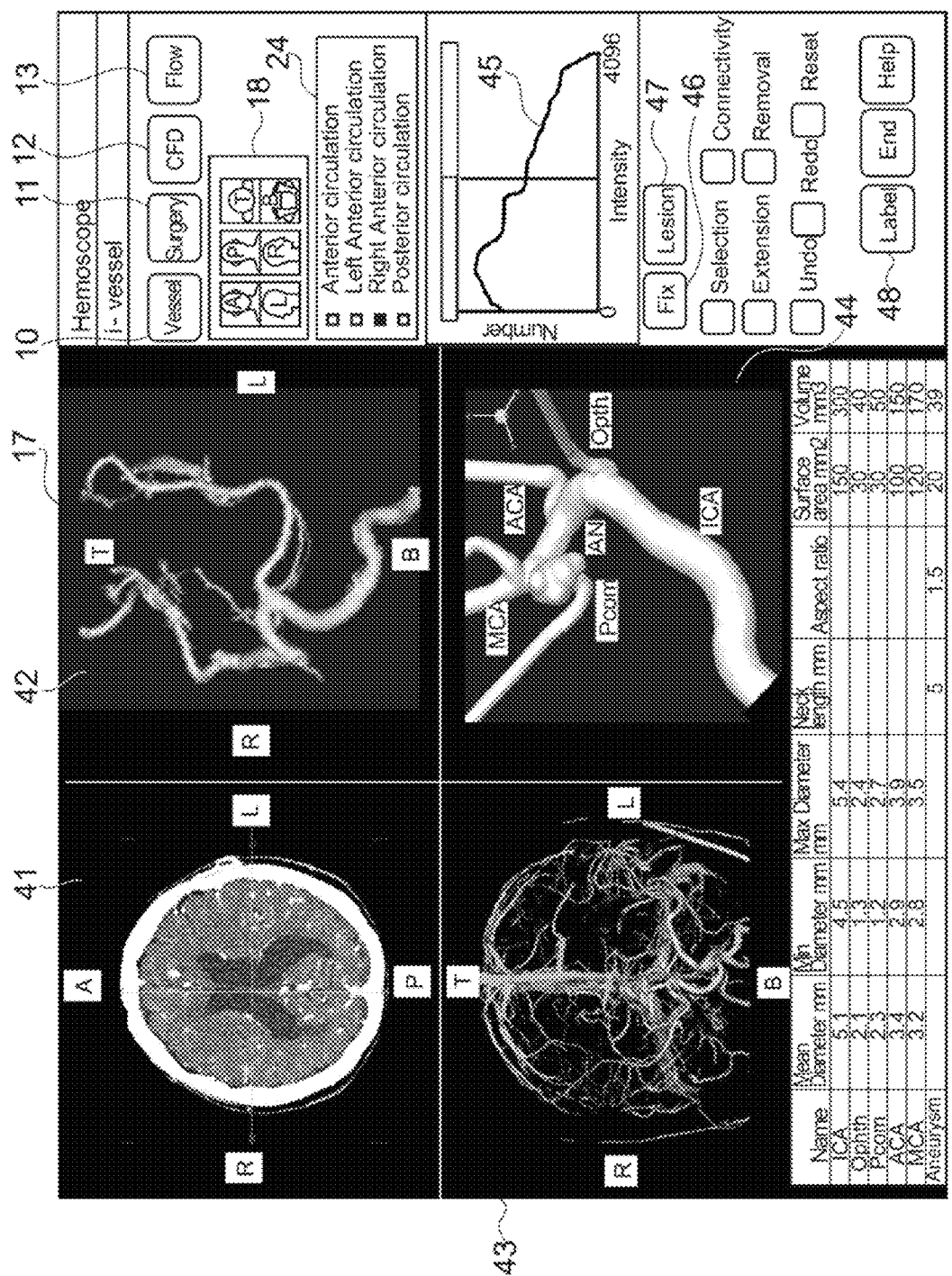
FIG. 2 depicts the graphical user interface of the vascular shape extraction unit.

FIG. 2 depicts the user graphical interface (GUI) 17 that is created by employing the display unit 14 of the server 3, and displayed on the user terminal 2. This interface configures an integrated interface function that operates the vascular shape extraction unit (i-Vessel) 10, the surgical simulation unit (i-Surgery) 11, the fluid analysis unit (i-CFD) 12, and the blood flow characteristics determination unit (i-Flow) together.

For example, FIG. 2 shows an example when the vascular shape extraction unit "i-Vessel" 10, whose function is described below, is selected from the menu located at the top of the display screen. In a similar fashion, the interface (to be described hereinafter) may switch the function by selecting i-Surgery 11, i-CFD 12, or i-Flow 13.

There was no such integrated system in the prior art where simply assembled individual systems through separate interfaces were used. A conventional system is anticipated to have technological difficulties in practical clinical applications and standardization of the analysis conditions because: (1) a user has to employee a plural number of systems one after another in order to analyze a single case while spending at least several hours in a workplace, and (2) each system is designed to have large flexibility and versatility for engineering work flows by adjusting many and different parameters for setting up an analysis routine, requiring user's knowledge and skill to optimize the parameters, which may not be suitable for medical applications.

This embodiment of the blood flow characteristics determination/treatment effect prediction system needs to be used as part of medical treatment in an extremely busy clinical environment. Therefore, the time restriction imposed on a medical practitioner and the inconsistency of analytical conditions among different users and facilities are major technical issues to be solved. It also needs to consider the factor to be included that a user, who is a clinical doctor or a radiology technician, is not an engineer and unaware of the knowledge of fluid dynamics. The embodiment of this system integrates the system units and a single interface 17 may execute an automatic control process, which eliminates the technological issues described above.

The embodiment of the system holds the optimal values of a group of the operational conditions for each application as a "module", which allows a user to carry out an automatic control process for a blood flow analysis required for a particular user's application without setting the group of the operational conditions.

Figure 3:
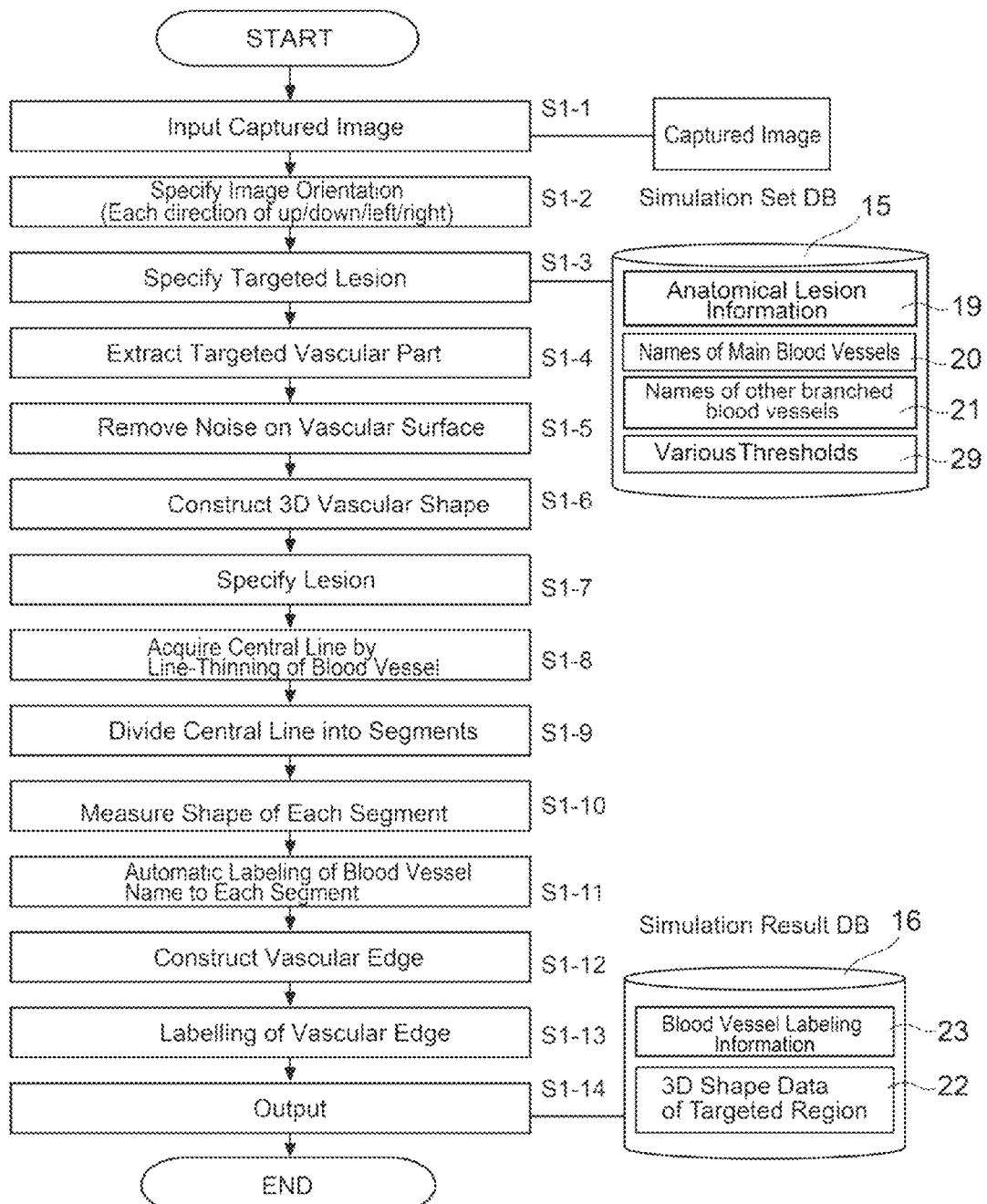
FIG. 3 shows a flow chart of the vascular shape extraction unit.

(Vascular Shape Extraction Unit) FIG. 3 shows a flow chart of the process steps of the vascular shape extraction unit, and FIGS. 4 to 9 illustrate vascular images that explain the process steps.

Step S1-1 inputs a set of image data, which an image capture device acquired from the target vascular site, in the DICOM format. Step S1-2 recognizes the orientation of the image (i.e., up, down, right, and left of the image) automatically or specifies the orientation manually. As described above, FIG. 2 depicts the user interface of the vascular shape extraction unit (i-Vessel). The interface that recognizes the image orientation is the display part 41 which is one of four display parts 41 to 44 and located in the upper left corner of FIG. 2. As the display parts 42 and 43 show, when a three-dimensional vascular shape is visualized by applying a volume rendering method known to those skilled in the art, the orientation of the blood vessel to be displayed may be specified by pushing "Anterior (A)", "Posterior (P)", "Left (L)", or "Right (R)" of a button 18 so that the vascular image orientation is aligned with the direction of "Anterior (A)", "Posterior (P)", "Left (L)", or "Right (R)".

Next, on the same screen (FIG. 2), an anatomical part is specified by selecting, e.g., a radio button 24 (Step S1-3). The anatomical part specified in this step is used for labeling blood vessels automatically in a step described hereinafter. For example, if a cerebral aneurysm is found in the right middle cerebral artery (MCA), "Right Anterior Circulation" is selected. Similarly, "Left Anterior Circulation", "Anterior Circulation", or "Posterior Circulation" may be also selected. The item 19 shown in FIG. 3 indicates that the anatomical part is stored in the simulation setting DB 15.

Step S1-4 and following steps construct the three-dimensional vascular morphology (the three-dimensional shape data) by applying the threshold method or the gradient method combined with the region growing method (and other methods shown in FIG. 2, including: the "Selection (where a user specifies a region of interest on screen to determine a region containing a targeted blood vessel from a three-dimensional structure that is extracted by applying the threshold method (or the gradient method))", "Connectivity (where the user specifies the targeted blood vessel to extract the targeted blood vessel by selectively taking continuous voxels only)", "Extension (which is an region growing method including the threshold method (or the gradient method) and the continuity of voxels, and adds blood vessels that need to be used but deleted in the blood vessel extraction Step)", and "Removal (where the user deletes the blood vessels that is not required)." For this purpose, Step S1-4 extracts a targeted vascular region. The extraction is executed by using e.g., the threshold or the gradient method.

Figure 4:
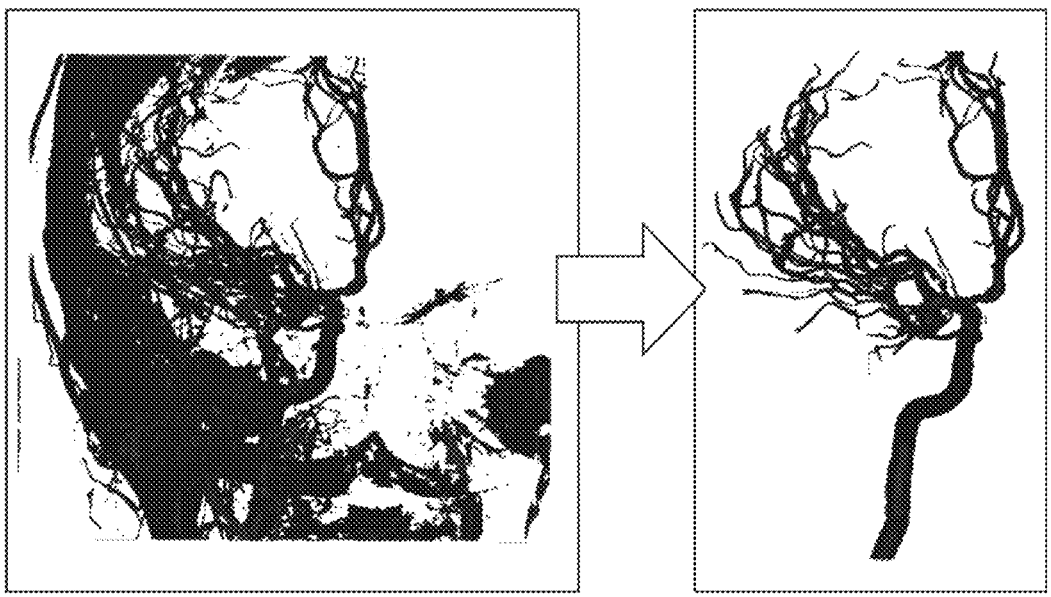
FIG. 4 illustrates a vascular image that explains the extraction of a vascular shape image.

FIG. 4 shows an example of the extraction using the threshold method.

The threshold method uses, for instance, the absolute value or the normalized relative value of luminance. In this embodiment, the threshold setting unit 45 applies the slider method to select the histogram threshold value and changes the threshold value while observing the image on the display unit 42 to extract the characteristics that are intrinsic to the vascular wall. On the other hand, the gradient method calculates the luminance gradient of the brightness from the luminance distribution. After the extraction step, a user pushes the "Fix" button 46 on the screen shown in FIG. 2 to activate the vascular shape extraction unit 10 to remove noise from the vascular surface by using the optimal threshold value for a given image type (Step S1-5), and then construct three-dimensional shape data by dividing the region into polygons to complete extracting the targeted vascular region (Step S1-6). FIG. 4 depicts a schematic diagram of extraction of vascular morphology in this step. These threshold values are stored in the simulation setting DB 15 (the item 29 shown in the figures attached therein).

Figure 5:
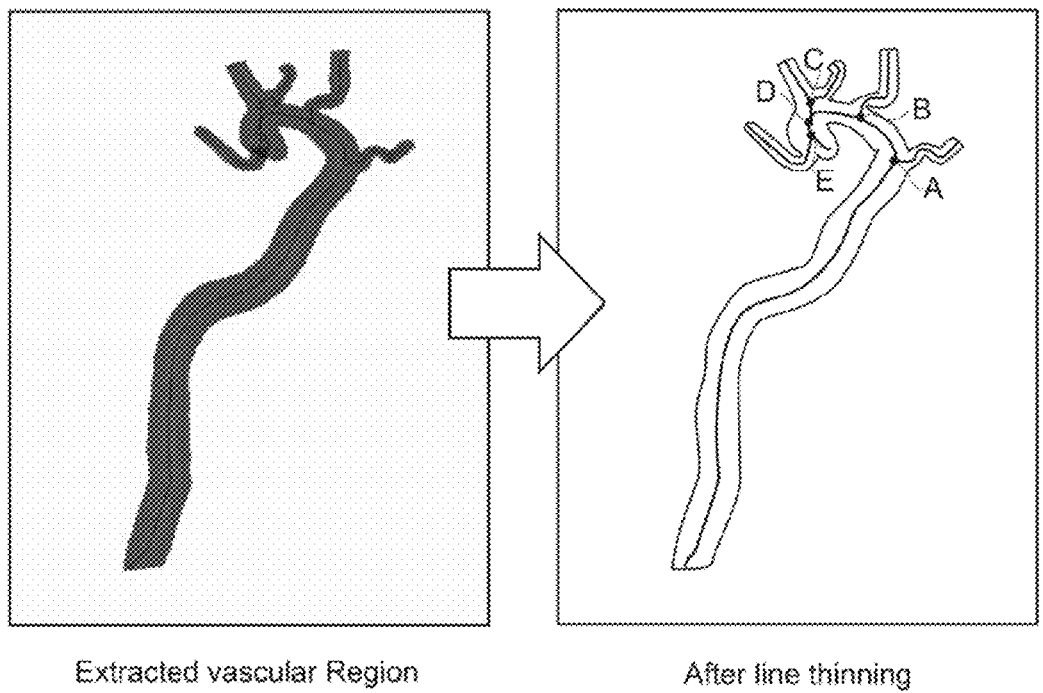
FIG. 5 depicts the line-thinning step for vascular shapes.
Figure 6:
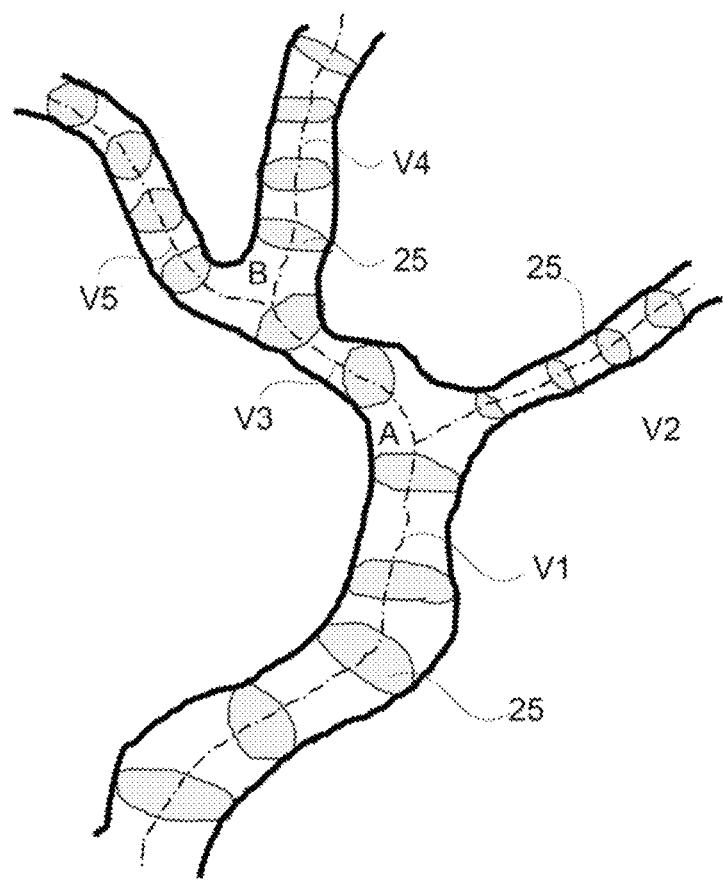
FIG. 6 illustrates labeling the name of blood vessels including the main blood vessels.

Then, a user presses the "Lesion" button 47 on the screen shown in FIG. 2 by using a device such as the mouse to specify the lesion manually (Step S1-7). Step S1-8 executes the line thinning routine to create the center lines of blood vessels. A user may automatically perform the line thinning routine by pushing the "Label" button on the screen of FIG. 2. There are various well-known algorithms for the line thinning routine. FIG. 5 shows the actual line thinning step. After acquiring the center lines, Step S1-9 divides the center lines into multiple segments each of which corresponds to a blood vessel. As shown in FIG. 5, the segment-division routine may be performed by segmenting the center lines at vascular bifurcation points A, B, C, D, etc. FIG. 6 enlarges the segmented regions. In this figure, the segments (V1, V2, . . . ) between two adjacent bifurcations, A, B, C, . . . , are called the blood vessel elements. Step 1-10 obtains several cross-sectional areas (as shown in FIG. 6) that are perpendicular to the center line of each blood vessel segment, and then calculates the equivalent diameter of the cross-sections for measuring the shape 25 of each segment.

Step S1-11 labels the name of each blood vessel segment automatically. Among the several blood vessel segments V1, V2, V3, . . . , the one that has the largest median of the various equivalent diameters calculated from the cross-sections 25 is determined to be the main blood vessel and labeled the name. (The mean value may not accurately represent the main blood vessel if there is an extraordinary large diameter due to a cerebral aneurysm in the blood vessel.) In this embodiment of the present invention, the labeling routine may be executed automatically as the anatomical lesion is specified. In other words, if the left anterior circulation is selected, the main blood vessel, (which is the blood vessel segment with the largest median of the equivalent diameters) is labeled the "left internal carotid artery" whereas, if a posterior circulation is selected, the main blood vessel is labeled the "basilar artery." These main blood vessels are identified as the ones with the largest equivalent diameters. Shape parameters other than the equivalent diameter or their combinations may be applied for the labeling routine. As shown in FIG. 3, the simulation setup DB 9 stores the anatomical lesion information 19, the names of the main blood vessel 20, and the names of branched blood vessels 21, as related to each other, which the labeling unit 35 of the vascular shape extraction unit 10 uses as "a labeling template" for the automatic labeling routine.

Thus, Step S1-11 performs the aforementioned labeling routine for the main blood vessels V2, V3, . . . , followed by tracking the branched blood vessels individually to label the names of blood vessels at each branch by identifying them according to the information stored in the DB 9. In the embodiment of the present invention, labeling the branched blood vessels is limited to carry out down to a 5 to 10 sub-layers from the main blood vessels. As described herein, once the name of the main blood vessel 20 is determined according to the information DB 19 of each anatomical lesion, the labeling routine of the branched blood vessels may be automatically performed by following the relation between the main blood vessel name 20 and the branched blood vessel names 21, which is stored in the database 9.

Figure 7:
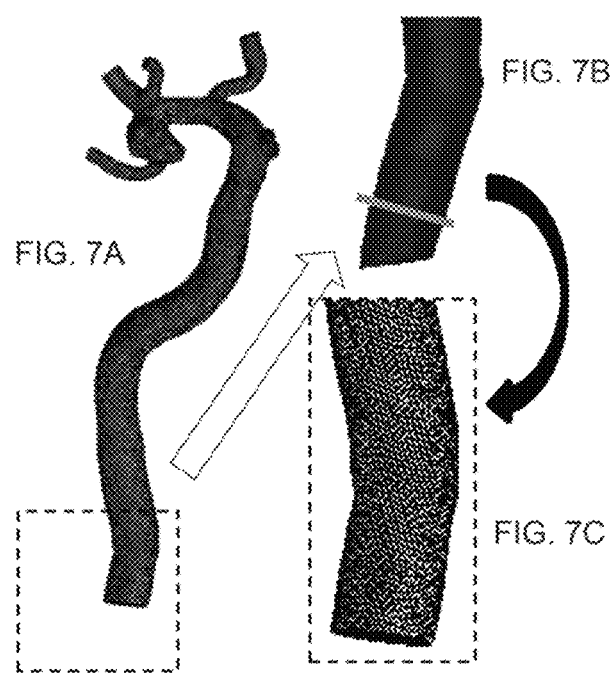
FIG. 7 shows processing of edging the extracted vascular shape.

Next, Steps, S1-12 and S1-13, after labeling, construct the cross-section of a blood vessel by making the inlet and the outlet of the blood vessel perpendicular to the central line based on the orientation (the vertical and the horizontal directions) of an image and the anatomical lesion specified as the targeted blood vessel that is selected in Step S1-2. FIG. 7 illustrates the cross-sectional construction. Step S1-4 automatically outputs polygon data as the three-dimensional shape. At the same time, the shape data 22 of each blood vessel (which is called the labeling information 23), which are labeled automatically, are calculated and recorded into the simulation result DB 16 automatically (FIG. 3). A user may confirm if the process is appropriate by checking the interface 17 displayed on screen. There may be a case where labeling is not processed properly in the automatic process. For example, there is a case where a patient with a congenital vascular malformation would not have a blood vessel at a corresponding location. In such a case, the diagnostic simulation system may be configured so that clicking on the falsely labeled blood vessel changes the name of the selected blood vessel. The names 20 and 21 of the setting DB21 may be also changed at this time. After the manual process, clicking the <End> button outputs the result automatically and overwrites to update DB15 and DB16. The name of a file output is configured according to the patient ID that may be extracted from the DICOM header information with which the file format may be obtained, which allows a user to eliminate inputting the file format manually. The surgery simulation unit 11, the fluid analysis unit 12, and the blood flow characteristics determination unit 13 have the same file name protocol as described hereinafter.

Figure 8:
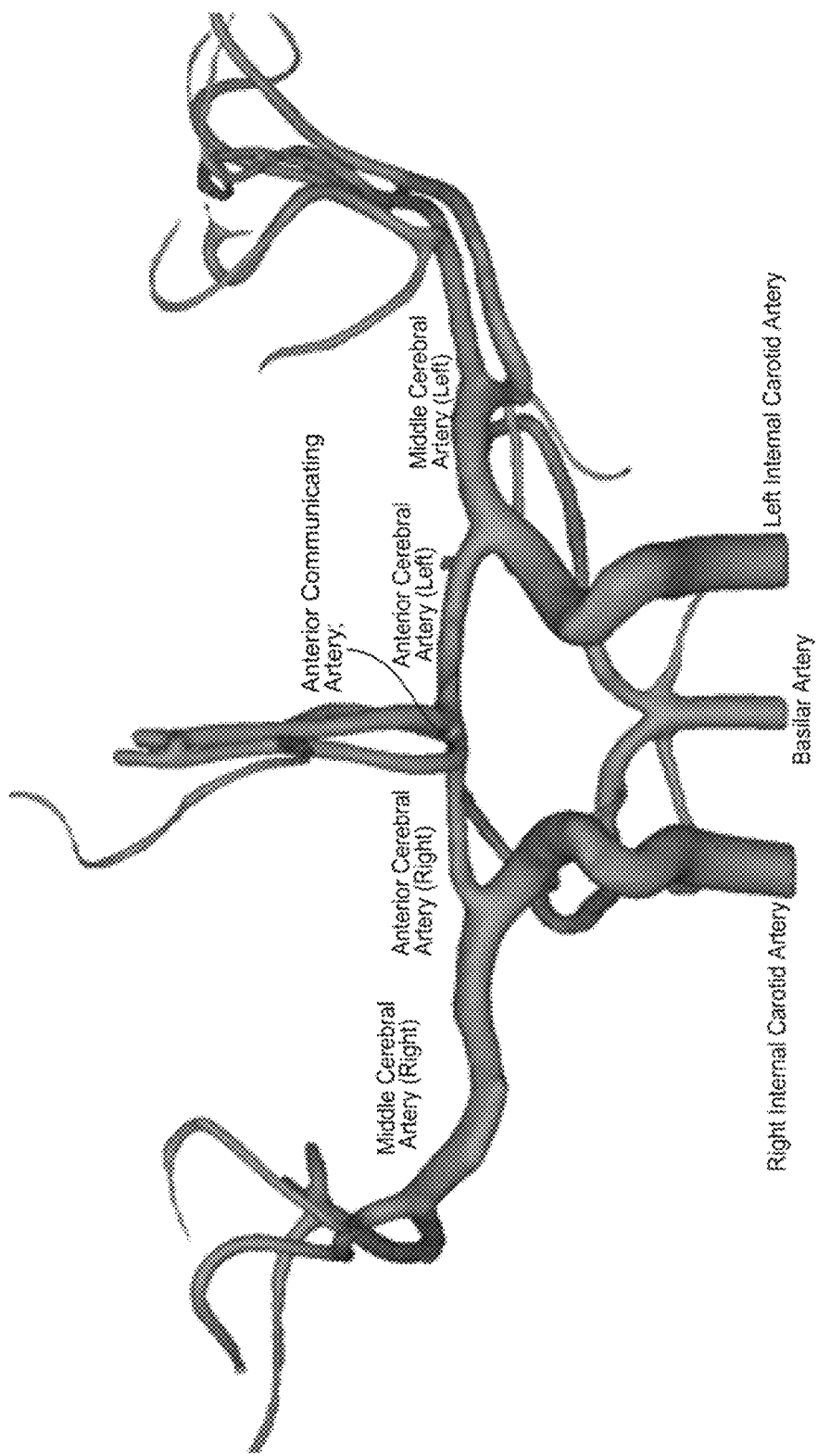
FIG. 8 shows a schematic diagram of overall shape of blood vessels in a brain.

FIG. 8 overviews a list of the names of cerebral blood vessels. FIG. 8 is for the anterior and the posterior circulations. For example, the anterior communicating artery, a lesion where cerebral aneurysm often appears, runs across the left and the right anterior circulations, and hence it is necessary to target the overall anterior circulation for analysis.

(Surgery Simulation Unit)

Figure 9:
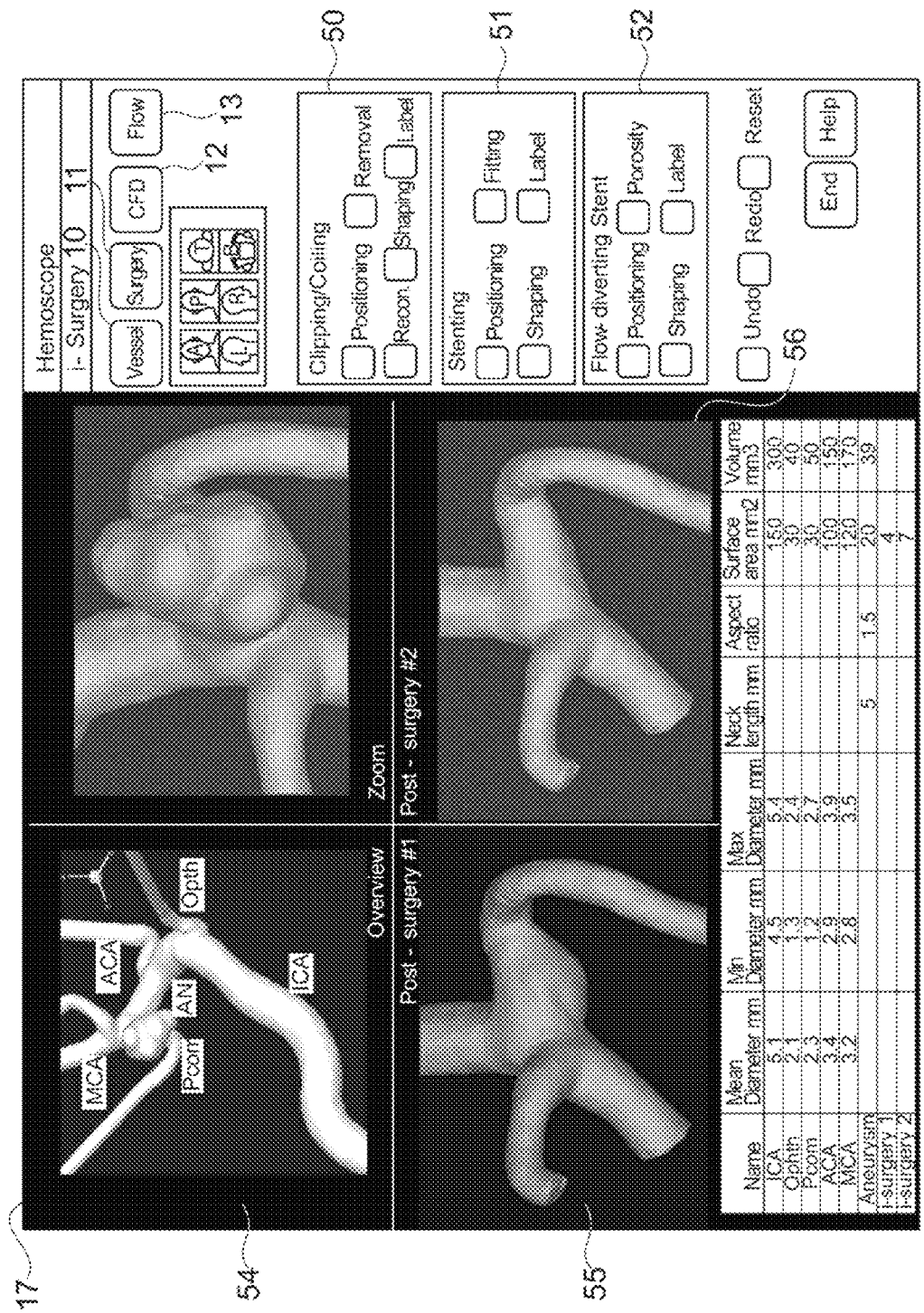
FIG. 9 depicts the graphical user interface of the surgical simulation unit.
Figure 10:
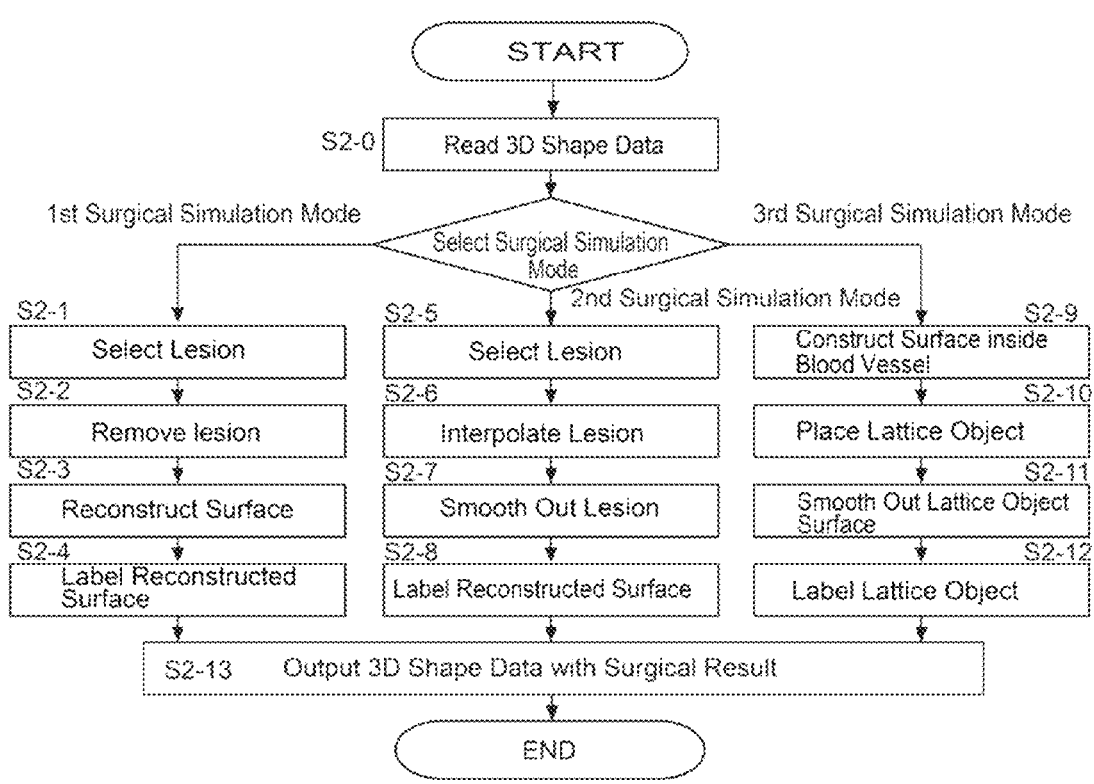
FIG. 10 illustrates a schematic diagram of the surgical simulation unit.
Figure 11:
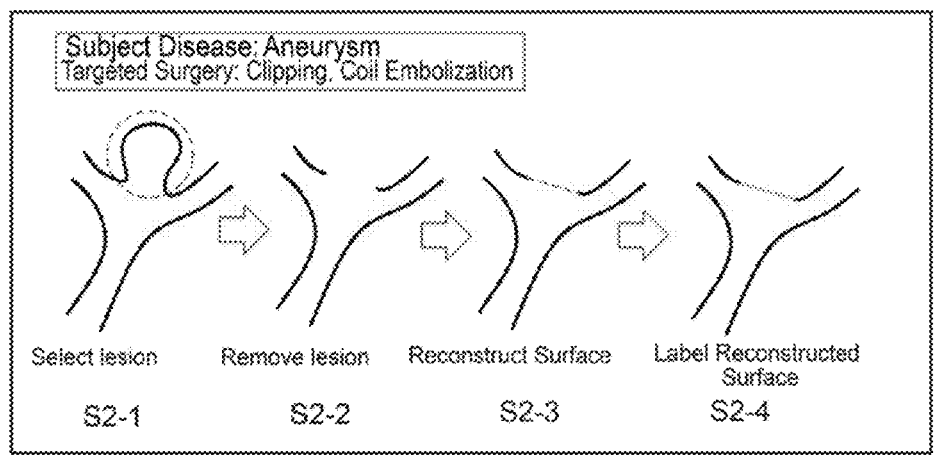
FIG. 11 depicts a simulation in the first surgical simulation mode.
Figure 12:
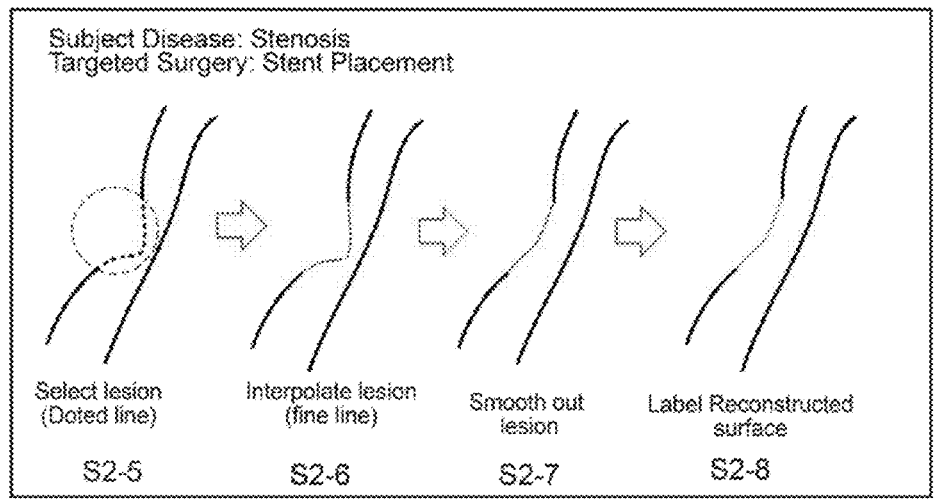
FIG. 12 depicts a simulation in the second surgical simulation mode.
Figure 13:
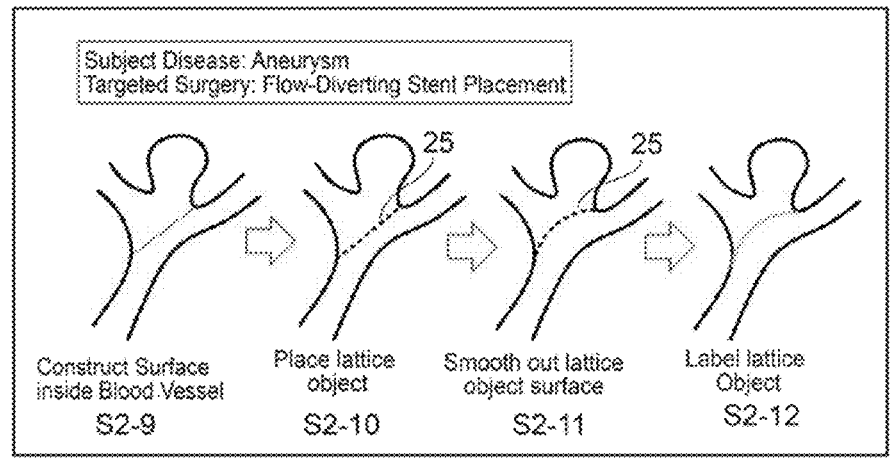
FIG. 13 depicts a simulation in the third surgical simulation mode.

FIG. 9 depicts a schematic diagram of the user graphical interface 17 of the surgery simulation unit 11; FIG. 10 shows the operational flow chart of the surgery simulation unit 11; and FIGS. 11, 12, and 13 illustrate the surgical modes. FIG. 14 is a schematic diagram of the shape modification unit 34 that modifies the three-dimensional morphological unit for the surgical simulation.

In this example, the interface 17 shown in FIG. 9 allows a user to select a surgical mode from the three predetermined modes, "Clipping/Coiling" 50 as the first surgical mode, "Stenting" 51 as the second surgical mode, or "Flow-diverting" as the third surgical mode. With this surgical mode selection, the surgical simulation unit 11 may produce the optimal vascular shape to reproduce the post-surgical blood flow.

In the aforementioned three modes, the first surgical simulation mode cuts out a lesion and reconstructs the vascular wall surface (Clipping/Coiling); the second surgical simulation mode reconstructs the vascular surface by smoothing the uneven surface of the lesion (Stenting); and the third surgical simulation mode places a lattice like object on an arbitrary vascular cross-section (Flow-diverting stent).

The vascular shape modification method (the item 37 in FIG. 15) corresponding to the first surgical simulation mode is a program group 50 (consisting of <Positioning>, <Removal>, <Recon>, <Shaping>, and <Label>) that simulates surgical clipping or coil embolization that completely closes an aneurysm lumen, in order to conduct a pre-surgical estimation of the fluid force which exerts on the neck of aneurysm formed by the surgery. The vascular shape modification method corresponding to the second simulation mode is a collection of programs 51 (consisting of <Positioning>, <Fitting>, <Shaping>, and <Label>) which simulates a stent placement that enlarges a vascular stenosis due to arteriosclerosis by employing a medical device such as a stent to conduct a pre-surgical estimation of the fluid force which exerts on the lesion formed by the surgery. The vascular shape modification method corresponding to the third surgical simulation is a collection of programs 52 (consisting of <Positioning>, <Porosity>, <Shaping>, and <Label>) which simulates a treatment of cerebral aneurysm by using the flow-diverting stent to estimate the effect of reducing the flow through the aneurysm.

Figure 15:
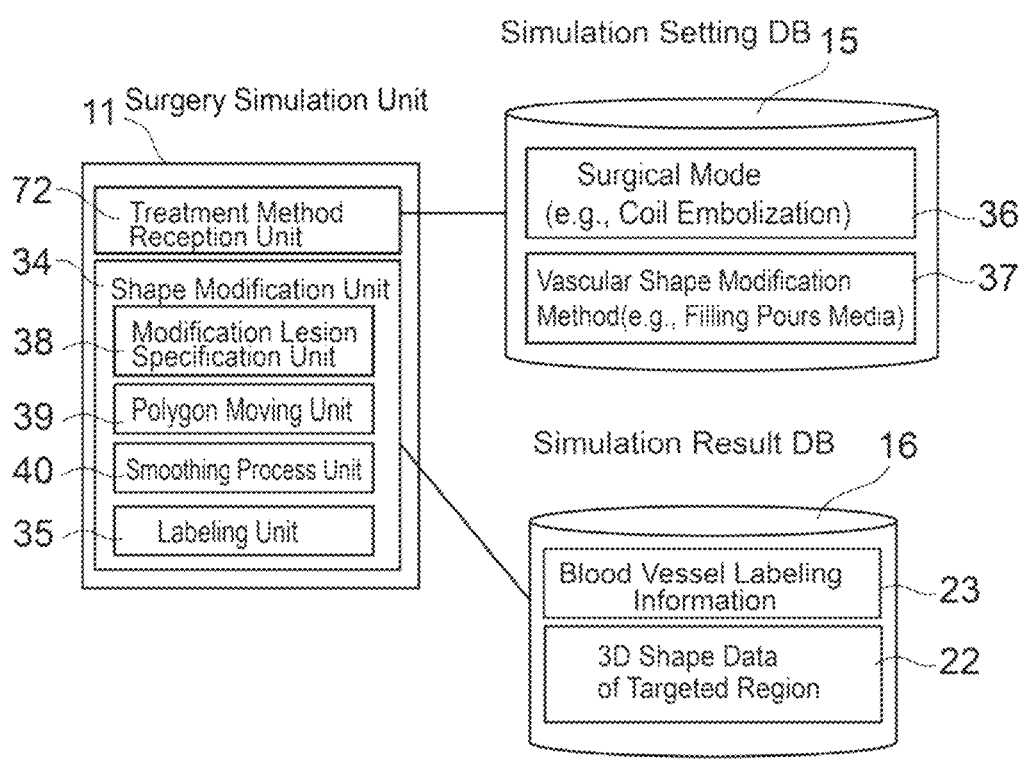
FIG. 15 shows a schematic diagram of the fluid analysis unit.

This simulation is conducted by actually modifying the three-dimensional vascular shape data, and the surgical simulation unit has the treatment receiving unit 73 and the shape modification unit 34 as shown in FIG. 15. Below is a description of the unit configuration along with their processing operations. The selectable surgical modes (which are the first to the third surgical simulation mode in this example) and the concrete methods for modifying the vascular morphology defined in relation to the surgical modes are stored in the simulation setting DB 15 as shown the items 36 and 37 in FIG. 15.

First, on the screen of the user graphics interface 17, a user pushes the <Surgery> button 11 to display the vascular morphology that is created by the vascular shape extraction unit through the browser display of the user terminal 2. (Step 2-0: the display part 54 on the upper left corner of FIG. 9.) When a user activates the first surgery simulation mode (the item 50 in FIG. 9) on the interface 17, the treatment receiving unit 73 loads the vascular shape modification method 37 (which is the program group 50 consisting of <Positioning>, <Removal>, <Recon>, <Shaping>, and <Label>) from the setting DB 15, and the user selects a lesion by using the <Positioning> (Step 2-1). If the user selects <Positioning>, the modified lesion specification unit 38 displays the specified region on the user interface 17. (The display part of the upper right corner of FIG. 9.) Because the three-dimensional shape data are polygon data that are a collection of minute triangles that configure the surfaces and the ends blood vessel surface and the ends of blood vessels, the specified region may be enlarged or shrunk for the purpose of the surgical simulation. If the user selects <Removal>, it cuts out the triangle element selected by the polygon moving unit 39 shown in FIG. 15 (Step S2-2). Pushing the <Recon> button reconstructs a surface on the dissected part by using polygons. Pushing the <Shaping> button activates the modification specification unit 38 and a user may activate the modification specification unit 39 and operate the mouse to carry out smoothing the reconstructed surface (Step 2-3), and then <Label> defines labeling the new surface (the Labeling unit 35) (Step S2-4). The surface reconstruction may be executed by calculating the center of mass of the dissected region and connecting it with the vertexes of the triangle elements at the edge of the dissected region. For smoothing the surface, a user freely move the center of mass of the triangle to the normal direction of the outer (or inner) peripheral direction of the dissected surface by pushing the mouse wheel button, i.e., shifts the center of mass which is the unique point of the triangle to a different location to distort the triangle artificially. A shape with an acute angle by moving the center of mass may be smoothed out simultaneously (by using the aforementioned units 38 and 39).

With the user interface shown in FIG. 9, a user uses the display parts 55 and 56, <<Post-surgery>>, at the left and right bottom to display an image of lesion after surgery and conduct surgical simulations using the program group. After completing the labeling step, <End> finalizes the shape, and similar to the vascular shape extraction unit, polygon data are stored automatically, updating the simulation result DB 16 (Step 2-13: Updates of labeling information 23 and three-dimensional shape data 22). For comparing a plural number of surgical simulations by repeating the previous steps, there are the display parts of <<Post-surgery>> at the right bottom 55 and at the left bottom 56 <<Post-surgery #1 and #2>>. (The comparison display part of the present invention).

Figure 14A:
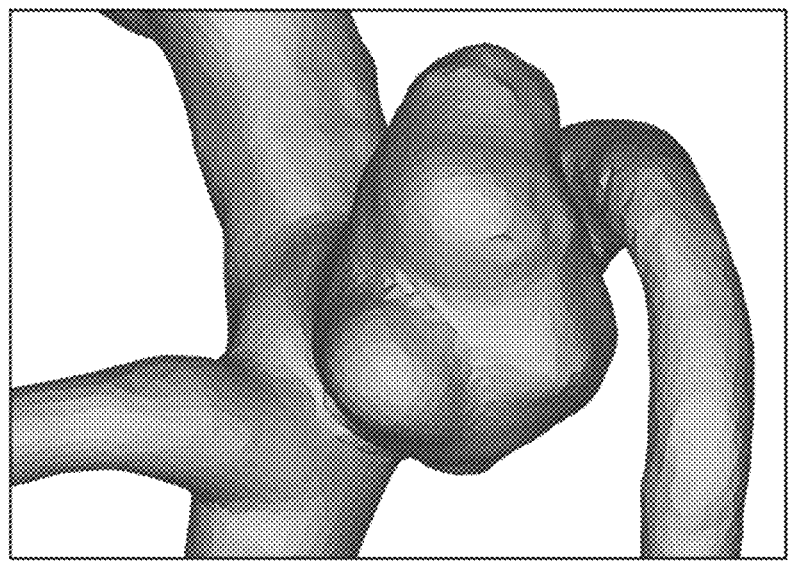
FIG. 14 illustrates an example of modification by applying the first surgical simulation mode.
Figure 14B:
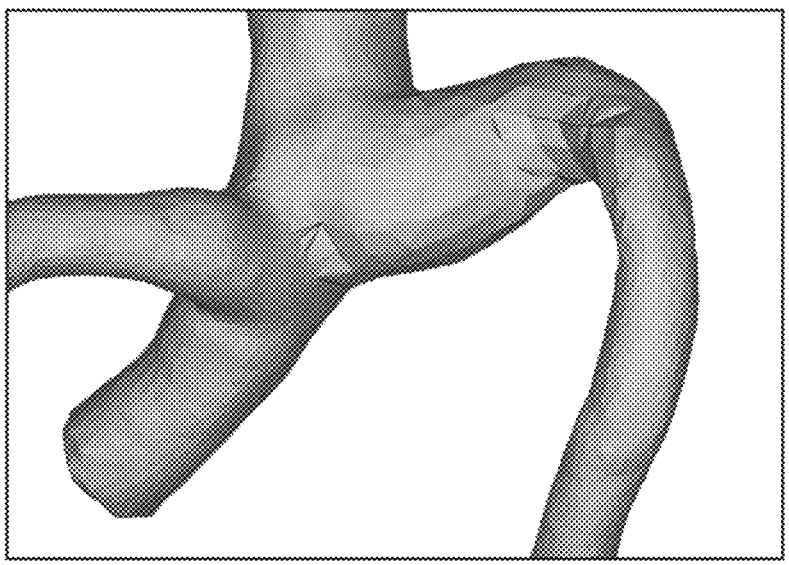

FIG. 11 depicts a diagram of an example of vascular shape modification in the first surgical simulation, and FIGS. 14A and B show the three-dimensional shape before and after the simulation (corresponding to before and after a treatment by clipping). As shown herein, deleting polygons that configure a shape of the cerebral aneurysm may reproduce three-dimensional vascular shape which exhibits the blood flow characteristics after conducting the clipping treatment. Therefore, a user may arbitrarily adjust the cross-sectional shape of a cerebral aneurysm that is constructed by a clipping treatment or a coil embolization in order to simulate and analyze the post-surgical blood flow.

In the second surgical simulation mode 51, similar to the aforementioned simulation, using <Positioning>, the lesion is selected and scaled-up and down (Step S2-5, the display part 55). In the next step, with <Fitting>, the center of gravity of the lesion is calculated, and using the center as the starting point, a polygon is moved in the normal direction to the vascular wall, and a polynomial fitting interpolates the lesion morphology (Step S2-6). Then, with <Shaping>, smoothing out of the lesion is executed using the mouse (Step S2-7), and finally, a method similar to the aforementioned first surgical simulation performs the labeling routine (Step S2-8). FIG. 12 illustrates a diagram of an example of the shape modification with the second surgical simulation.

In the third surgical simulation mode 52, a user uses <Positioning> to construct a new surface inside the three-dimensional vascular morphology (Step S2-9). Next, for a specified surface, <Porosity> defines a lattice-like object (Step S2-10), smoothing out the surface by applying a method similar to the aforementioned method (Step S2-11), and executes labeling (Step S2-12). The lattice-structured object used for the vascular shape modification method 37 (FIG. 15) attempts to simulate the flow-diverting stent. The lattice-structured object is a homogeneous porous media that a user may adjust the aperture ratio by using a pull down menu. The user may also create an inhomogeneous media by adjusting the aperture ratio and the shape of a pours media. FIG. 13 shows a diagram of an example of shape modification by the third surgical simulation mode. In this figure, the lattice-like object is the item 25. The blood flow simulation using the porous media may also simulate the blood flow after conducting a coil embolization surgery. The aforementioned coil embolization assumes a complete embolization in the lump. This actually corresponds to a condition of adequate embolization in the lump when the time subsequently elapsed after surgery. On the other hand, there is blood flow in the coil until it is completely blocked. Whether the blood flow may be simulated or not is crucial to determine the coil filling ratio (which is the volume ratio of the coil to the lump). The above-described flow-diverting stent uses the porous media as a two-dimensional structure, which may extend to the three-dimensional structure to simulate the condition immediately after a coil embolization. In other words, it is possible to add a function of simulating the coil filling ratio by using the aforementioned <Porosity> to place a porous media in the lump and simulate the coil filling ratio with the aperture ratio.

(Flow Analysis Unit)

In the next step, the fluid analysis unit 12 obtains the blood fluid velocity and pressure (which is the state variable 33) at each unit area of the target vascular site using the three-dimensional shape data of the target vascular site created by the vascular shape extraction unit 10 (and the surgical simulation unit 11).

Figure 16:
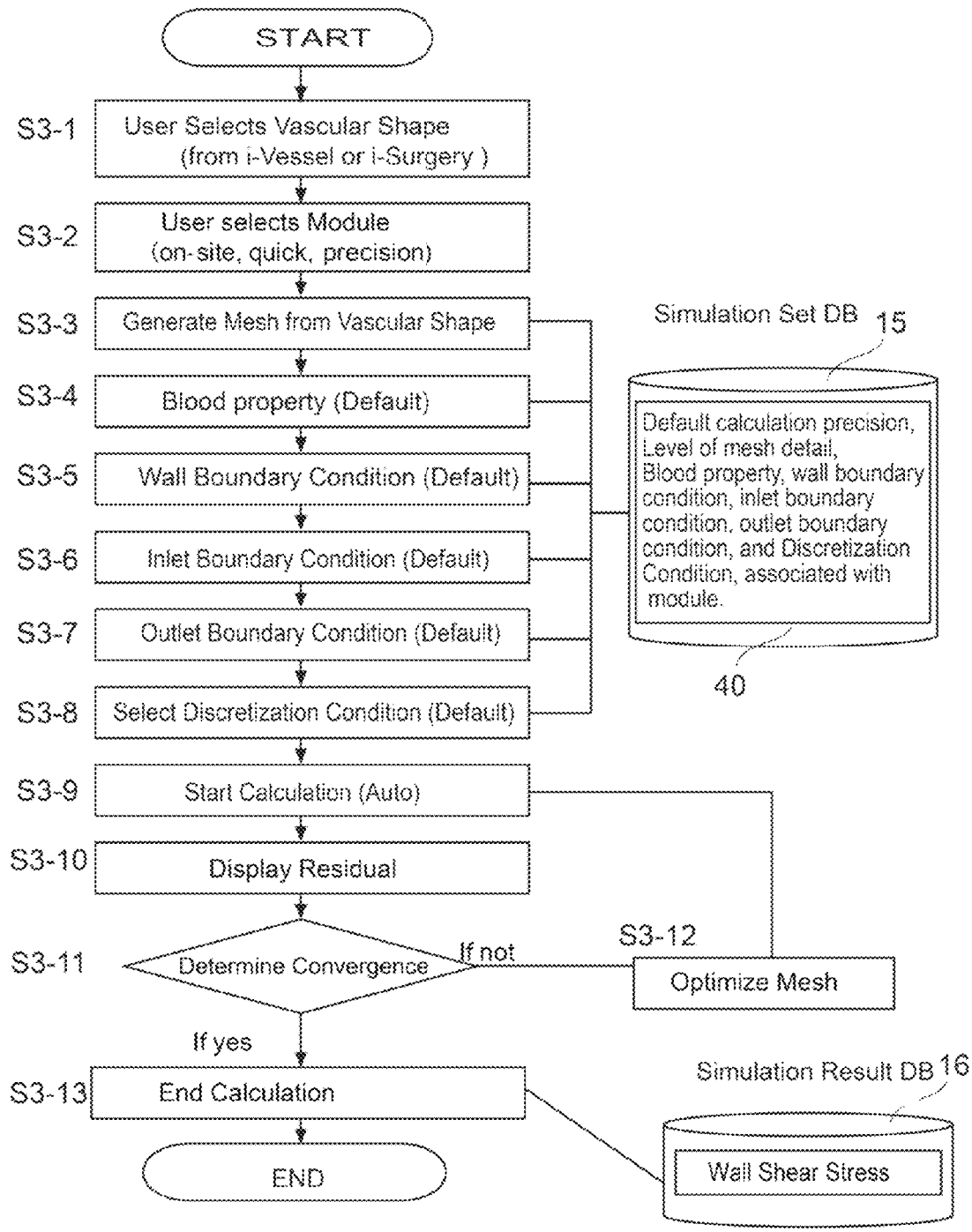
FIG. 16 shows a flowchart of processes performed by the fluid analysis unit.
Figure 17:
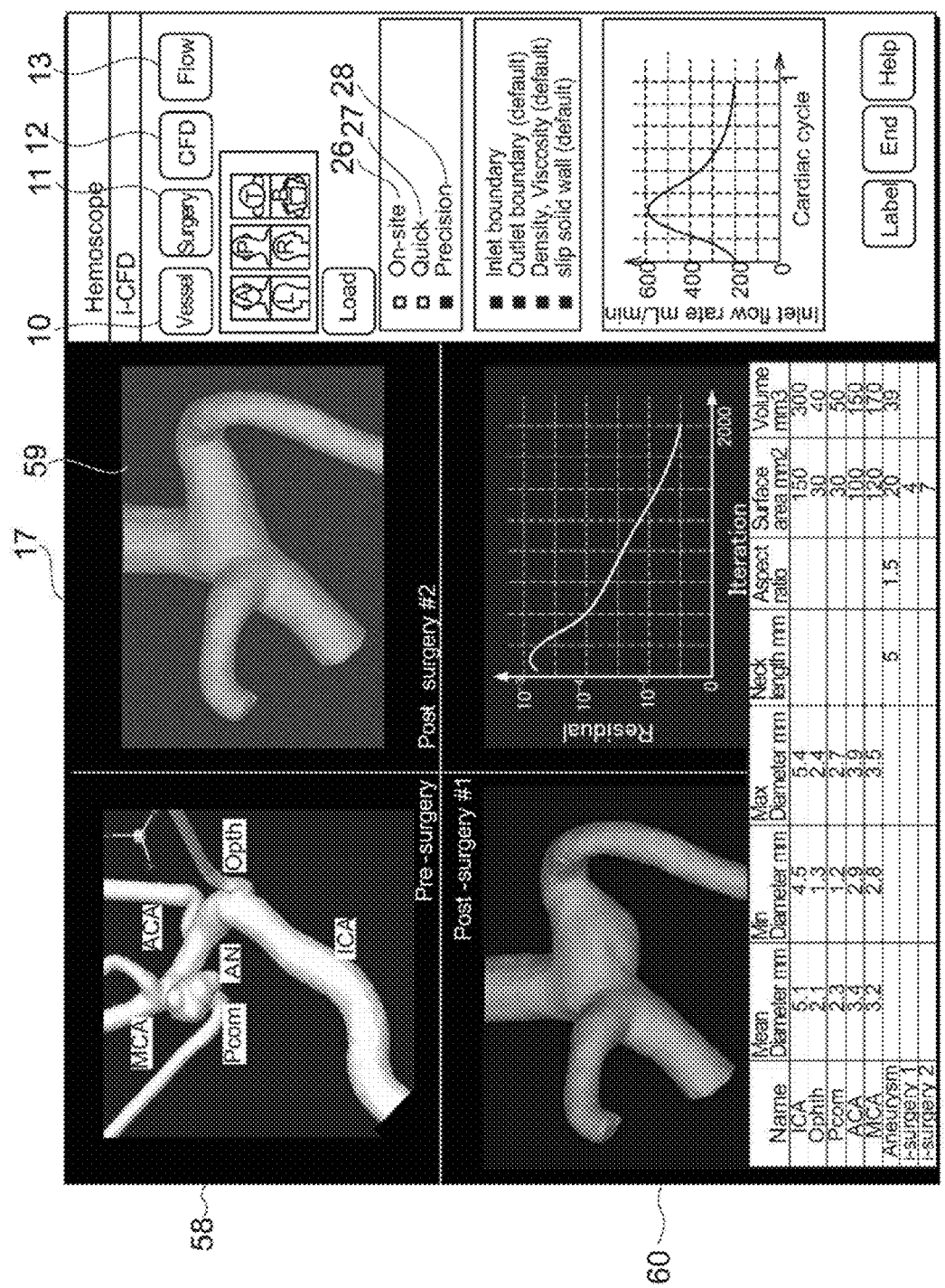
FIG. 17 depicts the graphical user interface of the fluid analysis unit.

FIG. 16 is the flow chart of processes that the fluid analysis unit 12 executes, and FIG. 17 shows an example of selecting "CFD" 12 from the menu of the user graphic interface 17.

In Step S3-1, the fluid analysis unit 12 selects and reads the vascular shape data for calculation from the three-dimensional shape data of the target vascular site which the vascular shape extraction unit 10 (and the surgical simulation unit 11). The selected data is displayed on the display parts 58, 59, and 60 which locate the upper left corner of the interface 17 as shown in FIG. 17. In this example, the display unit 58 displays the shape data of Pre-Surgery, the display part 59 displays the shape data of Post-Surgery #2, and the display part 60 displays the shape data of Post-Surgery #1.

In the next step, Step S3-2, a user selects a "module." As shown in FIG. 17, for selecting a "module", there are three buttons displayed on the user graphic interface 17 and available for selection: "On-site" 26, "Quick" 27, and "Precision" 28.

The system configures a default set of mathematical operation values 40 (FIGS. 1 and 16) to execute computations with appropriate condition and precision after a user selects a module from the three modules. Considering the time restriction in the clinical practice and the user's non-expertise of the fluid analysis, this configuration of integrating the analysis conditions is realized to fulfill the demand from the workplace, and to achieve reproducibility and standardization of the analysis conditions. The mathematical operational condition for "On-site" adopts a steady flow analysis. The blood flow is an unsteady flow which is called the pulsatile flow produced by the cardiac pulsation. Calculation of an unsteady flow executes an iterative calculation that converges the solution at each time interval for the time-varying flow, which requires a large calculation load on the mathematical operation unit. On the other hand, the steady flow is not necessarily quite different from the pulsatile flow. In particular, the cerebral blood vessel is a region where the Reynolds number of the blood flow is relatively small, whence the blood flow is laminar in the pulsatile period, and does not have the transient vortex observed in turbulence with a large Reynolds number. In other words, the blood flow in the pulsatile period has a strong similarity in the variation of flow rate. Therefore, if a blood flow corresponding to the time-averaged flow may be reproduced, it is possible to understand the flow patter as the pulsatile flow. The On-site module is an analysis method that is supported by the experimental and analytical data of this approach.

On the other hand, "Quick" and "Precision" have the set of mathematical operation condition values 40 for the pulsatile flow. Unlike "Quick", "Precision" sets a condition with a capability of dealing with a change from the laminar to the turbulent pulsatile flow. The set DB 15 pre-stores various conditions, including the level of detail of mesh, the physical property of blood, the wall boundary condition, the inlet boundary condition, the outlet boundary condition and the discretizing condition, as the set of mathematical operation condition values 40. It would often take several days for a single fast processor to complete analyzing "Precision." In the embodiment of the present invention, the first processor 41 of the fluid analysis unit 12 executes the relatively light process of the On-site while the second processor 42 of a fast processing center 9 in a remote area carries out the heavy process of the Precision. In other words, the precision module is configured in order to perform the following job flow: the data for processing the Precision task is automatically transferred to the process center outside a hospital through a telecommunication network, parallel-processed with a plural number of fast processors, and then returned the analysis outcome to the hospital through the network.

In Step S3-3 and following steps, a user pushes the Run button 62 of the interface 17 shown in FIG. 17 to select the set of the mathematical operation values 40 for a selected module, and automatically performs the calculation. Step S3-3 divides the target vascular site into a plural number of triangles of the finite element method based on the three-dimensional shape data. The embodiment of the present invention creates a mesh structure using the level of detail of mesh for the blood vessel size based on the vascular labeling conducted by the vascular shape extraction unit 10. In other words, in this embodiment, the set of the mathematical operational condition values 40 stores the level of detail of mesh for the mesh dividing in relation to the blood vessel name, or dynamically determines the level of detail of mesh according to the vascular cross-section. Thus, this system may read the level of detail of mesh out of the set DB 15 according to the labeling and use it for the mathematical operation. That is, each level of detail of mesh may be determined according to the module selected and the vascular type.

Figure 18A:
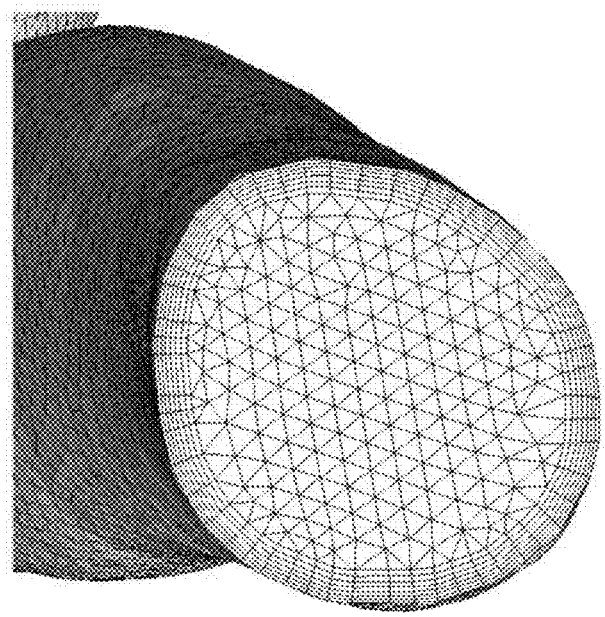
FIG. 18 explains the level of detail of mesh.
Figure 18B:
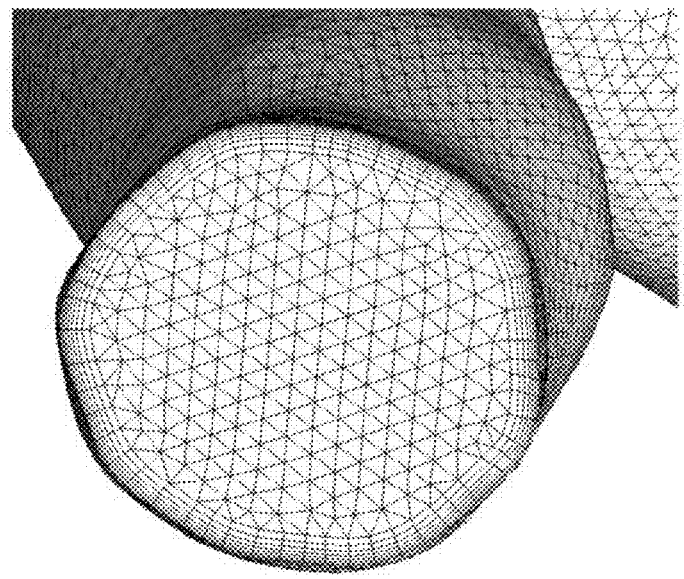

FIGS. 18A and 18B illustrate an example of varying the level of detail of mesh per blood vessel. In this example, the resolution for the ophthalmic artery of diameter 1 mm is set to be higher than the artery inside diameter 5 mm.

$D_{mesh}$ of this embodiment of the present invention is defined as follows.

$$D_{mesh} = D_{base} \times K_{scale} \times K_{module}$$

where $D_{mesh}$ is the level of detail of mesh (which is the representative diameter $D_{mesh}$ in this embodiment), $D_{base}$ is the size of the base mesh (which is a constant independent of the scale factor), $K_{scale}$ is a scale factor which varies according to the vascular size, and $K_{module}$ is a scale factor which varies according to the module selected.

An ordinary finite element analysis does not consider the scale factor defined above but determined the mesh size by the base mesh alone. For this reason, the prior art was unable to include the variation of each vascular diameter. However, the embodiment of the present invention may overcome the technological issue of the prior art.

An example is described hereinafter. In the example, the fluid analysis unit 12 calculates the equivalent vascular diameter D by using the blood vessel volume, the length of the central line of the blood vessel, and the approximate cylinder of the blood vessel for quantitating the vascular size.

1) For using the On-site, Quick module,
$D_{base}$=0.1 mm
$K_{scale}$=0.2 (if D<1.5 mm)
$K_{scale}$=1.0 (if D≥1.5 mm)
$K_{module}$=1

(In other words, in this module, the mesh size of the arteriole having the equivalent diameter D less than ⅕ mm is only refined to ⅕ of the base mesh.)

2) For using the Precision module,
$D_{base}$=0.1 mm
$K_{scale}$=0.2 (if D<1.5 mm)
$K_{scale}$=1.0 (if D≥1.5 mm)
$K_{module}$=0.5

(In this example, $K_{module}$=0.5 and the mesh is refined overall.)

With the above method, the mesh size would change abruptly at a vascular branch. The discontinuous change of the mesh increases the morphological distortion, which may lead to degrade the convergence of computation. For overcoming this computational issue, the embodiment of the present invention creates the mesh by using the aforementioned method, then providing the upper limit for the mesh distortion and repeatedly carries out the smoothing process so that the maximum distortion settles within the threshold value.

The analysis method of the prior art was unable to change the mesh size dynamically for the vascular size, and hence it used the same level of detail of mesh for both large and small blood vessels. Although a mesh size which is adequate enough to analyzing a large blood vessel conversely shows poor analytical precision for a small blood vessel whereas a mesh size adequate enough to analyzing a small blood vessel creates the level of detail of mesh unnecessarily to prolong the time for analysis, the present invention solves the technological problem.

The following steps S3-4 to S3-8 read out the set of mathematical operation conditions 40, which stores the physical property of blood, the boundary condition, and the analysis condition, from the aforementioned set DB 15, and Step S3-8 executes the mathematical operation based on these conditions. Specifically, the fluid analysis unit 12 solves a second order nonlinear partial differential equation that describes the motion of fluid, called the Navier-Stokes equation, by applying the finite element method, and obtains the fluid velocity and pressure at each mesh. In this case, the solution of the finite element method (the fluid velocity U and the pressure P) is obtained in the three directions, the X-global, the Y-global, and the Z-global, of the global coordinate frame.

In the mathematical operation conditions 40, the physical property of blood includes the viscosity and density. The boundary condition is the fluid conditions at the inlet and outlet of the targeted lesion for analysis and the fluid condition applies the statistical mean values of fluid velocity and pressure.

Although the set condition selects a default condition automatically according to the selected module as described above, this embodiment of the present invention preferably has an additional capability of manually inputting a condition into the fluid analysis unit 12 prior to execution of the mathematical operation.

After the calculation starts automatically, Step S3-10 displays the residual and the calculation repeats until the result satisfies the predetermined converging criterion. If the residual does not satisfy the predetermined converging criterion even after repeating the maximum number of iterations permitted, the calculation is determined to be non-converging (Step S3-11). In this case, optimization of the mesh distortion will be carried out (Step S3-12), and the calculation will be resumed. Once the residual reaches within the predetermined converging range, the completion of calculation is displayed (Step S3-13). The calculation result (which is the state quantities (U and P)) is automatically stored in the DB 16 in a similar manner described above.

The mathematical operation adopted herein is not only for the finite element method but also for numerical analyses of the differential equation of fluid flow, such as the finite volume method and the finite difference method.

(Blood Flow Characteristics Determination Device)

There is a software program that enables a computer to perform the following functions and installed in the blood flow characteristics determination unit 13. That is, as shown in FIG. 1, the blood flow characteristics determination unit 13 has the wall shear stress vector calculation unit 30 that obtains the fluid shear stress and its vector (the "wall shear stress vector", hereinafter) exerted on the vascular wall by the blood flow by using the fluid velocity and pressure for each mesh calculated by the fluid analysis unit, the flow disturbance index calculation unit 31 that obtains the numerical index (i.e., the flow disturbance index) from the wall shear stress vector, and the determination unit 32 that determines the blood flow characteristics at each mesh according to the flow disturbance index.

Figure 19:
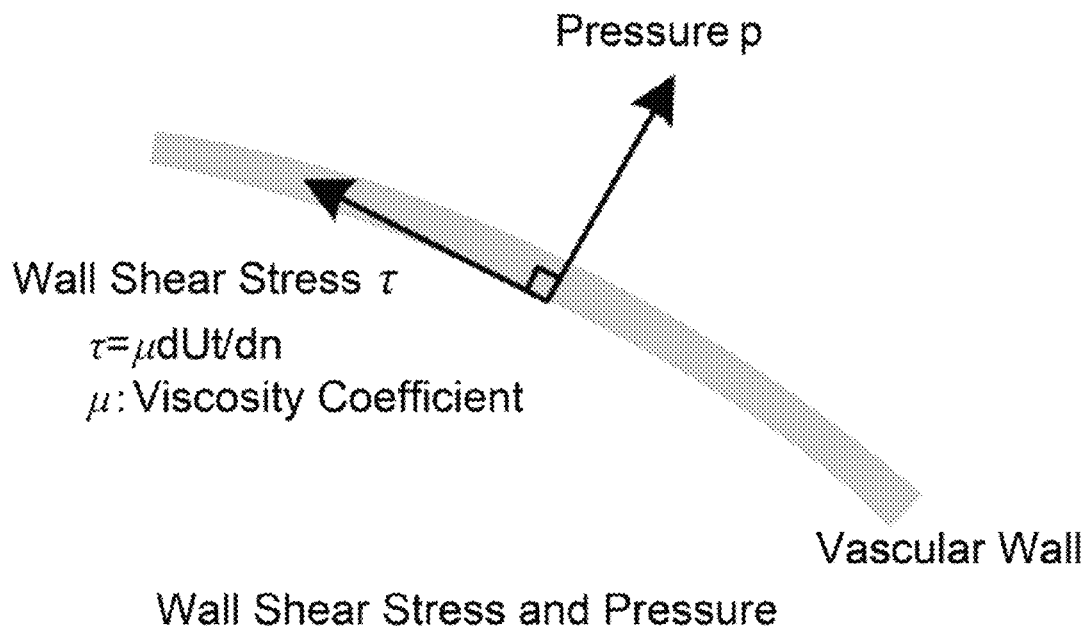
FIG. 19 illustrates a diagram of the fluid shear stress.
Figure 20:
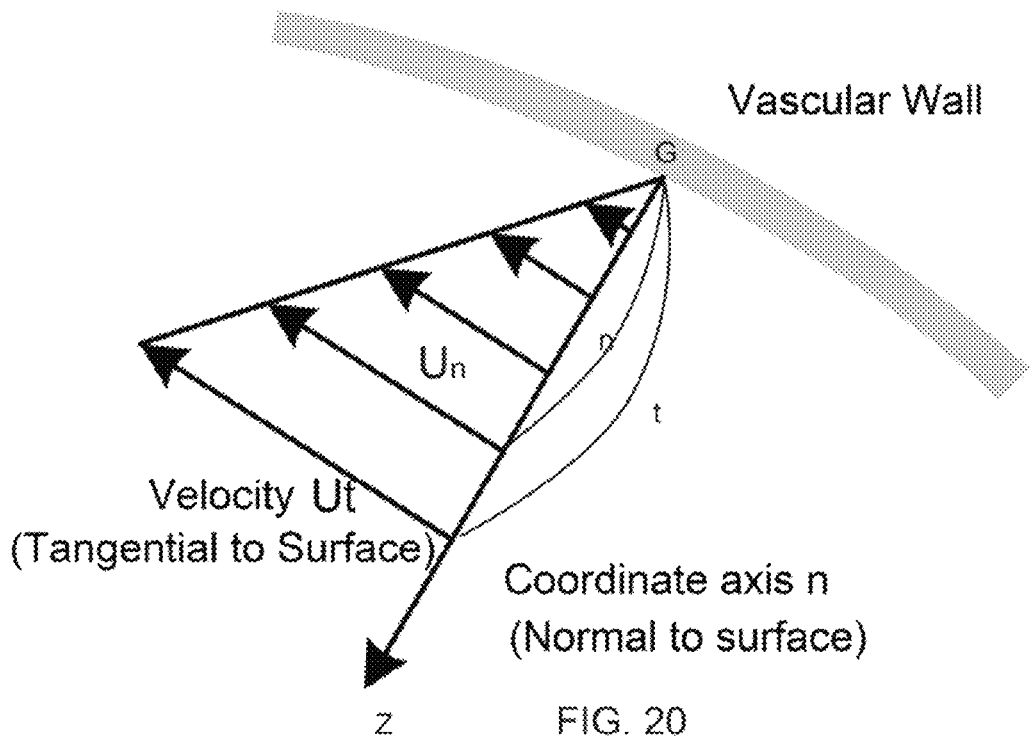
FIG. 20 illustrates a diagram of the fluid shear stress.

FIGS. 19 and 20 depict schematic diagrams to obtain the shear stress vector τ (x, y, z) based on the fluid velocity U and the pressure P obtained at each mesh in the wall shear stress vector calculation unit 30.

As shown in FIG. 19, the wall shear stress is the fluid viscous force exerting on an area element of the vascular lumen in the parallel direction, and the wall shear stress vector is the vector expression of the stress including the direction of the force. The acting direction of the wall shear stress vector is perpendicular to the pressure which is the fluid force exerting on the center of the mass of the area element in the normal direction of the area.

For describing the figure, it is necessary to understand the transformation from the global coordinate system to the local coordinate system. In other words, the pressure P and the velocity U for obtaining the shear stress vector are calculated in the global coordinate system whereas the shear stress force at a location on the vascular wall is in the tangential direction of the wall surface, and calculation of its magnitude requires transforming the pressure and the velocity from the global coordinate system to the local coordinate system of the vascular wall.

Figure 21:
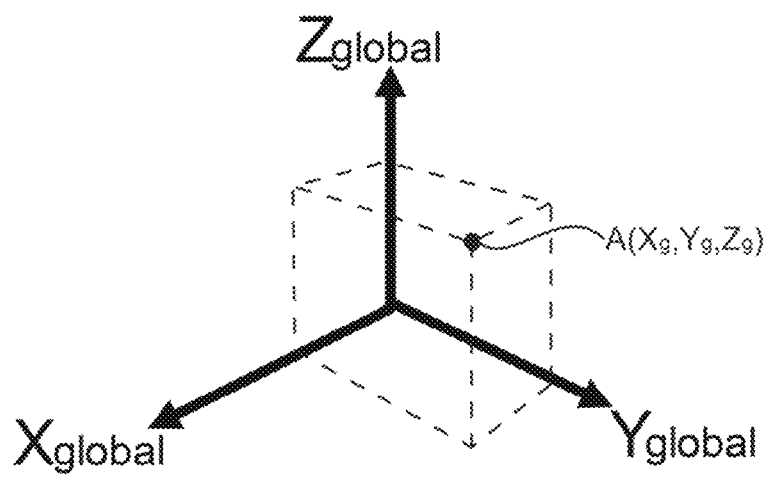
FIG. 21 shows the global coordinate system for calculating the wall shear stress.

Here, as shown in FIG. 21, the global coordinate system of this system of this invention is a unique reference coordinate to show a universal position of mesh nodes forming the vascular surface and lumen. The finite element method and the finite volume method represent the subject for calculation as a set of geometrical elements (such as triangle elements, tetrahedral elements, and hexagonal elements). Each element has a vertex called the node, and the position information is retained using the global coordinate system such as $(X1_g, Y1_g, Z1_g)$, $(X2_g, Y2_g, Z2_g)$, and $(X3_g, Y3_g, Z3_g)$.

Figure 22:
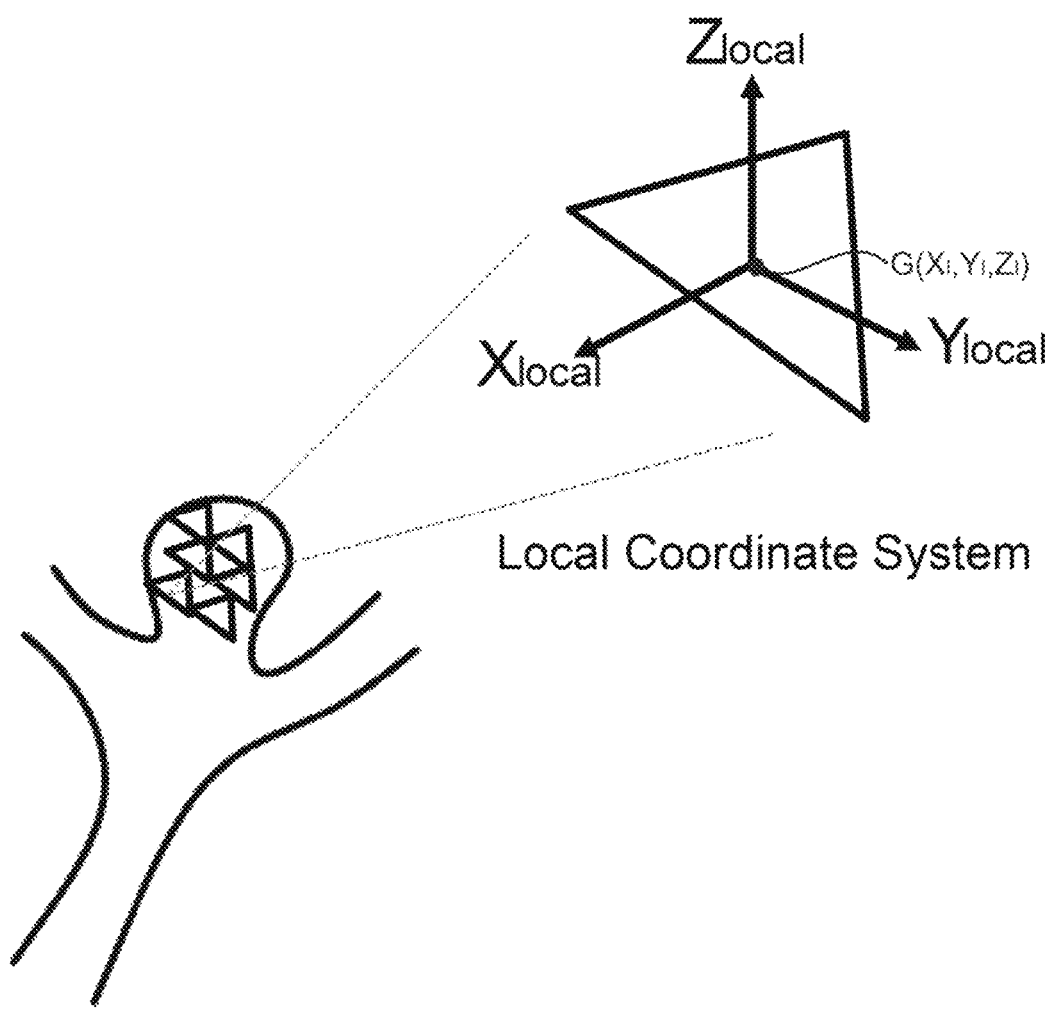
FIG. 22 shows the local coordinate system for calculating the wall shear stress.

As shown in FIG. 22, the local coordinate system is a frame of reference that is locally defined for each triangular element (or polygon) configuring the vascular surface, and usually, the center of gravity of the triangle is the origin and one axis (i.e., the Z axis) is taken to be the normal vector to the area. The local coordinates of each point of contact of the area element are $(X1_1, Y1_1, Z1_1)$, $(X2_1, Y2_1, Z2_1)$, and $(X3_1, Y3_1, Z3_1)$. The position in the global coordinate system and that of the local coordinate system may be mutually transformed by using the position of the center of mass of the triangular element and the direction of the area normal vector.

A method for obtaining the wall shear stress is explained below.

The first step is calculation of the velocity and the pressure at each node in the global coordinate system by using the output from the fluid analysis unit 12 (i-CFD). The next Step is specification of a triangle where the wall shear stress vectors to be calculated. The local coordinate system is configured for the specified triangular element. In the local coordinate system, a position G where the shear stress vector is calculated is determined. (For each triangular element, the distance from the wall is usually kept to be constant, e.g., 0.1 mm inward from the wall.) The fluid velocity at the position G is zero because it locates on the wall surface as shown in FIG. 20.

Letting Ut be the fluid velocity at a position from the position G by a distance t, which is assumed to be very small compared with the boundary layer thickness, in the normal direction (i.e., the Z direction of the local coordinate system), the fluid velocity Ut is approximately proportional to the distance n from the point G, and may be expressed as $$Un = n \cdot dUt/dZ.$$

According to the action-reaction law, the resistive force against moving the point at distance n at this fluid velocity has the same magnitude of the force that fixes the point, and both of them are proportional to the fluid velocity Ut and also inversely proportional to the distance Z. Therefore, the force τ per unit area at the point G in contact with the fluid becomes $$\tau = \mu \cdot dUt/dZ.$$

That is, the wall shear stress vector is the product of the viscous coefficient and the rate of changing the velocity vector parallel to the area element in the normal direction. There are several methods for calculating the changing rate of the velocity vector parallel to the area element in the normal direction. For example, it is possible to obtain the velocity at each point of a plural number of points on the Z1 axis by interpolating the surrounding velocity vectors. In this case, because the distance between the individual surrounding velocity vector and the candidate point is different, the interpolation requires a weight function of the distance. Since the surrounding velocity vector is expressed in the global coordinate system, the velocity vector after interpolation is expressed in the local coordinate system to calculate the velocity component parallel to the surface at each candidate point. When the changing rate in the normal direction is to be calculated later, the first order approximation using a single candidate point near the wall may be applied, or a higher order of mathematical differentiation where a polynomial approximation using a plural number of candidate points near the wall may be calculated followed by mathematical differentiation may be executed.

For calculating the aforementioned changing rate from velocity U(Xg, Yg, Zg) in the global coordinate system, the following approach may be applied: decomposing the velocity vector at the distance t in the local coordinate system (X1, Y1, Z1), and solving τ=μ·dUt/dZ in the coordinate (X1, Y1) parallel to the wall surface in each local coordinate system (the Z component is zero).

In other words, $$\tau(X1) = \mu \cdot dUt(X1)/dZ,$$

and $$\tau(Y1) = \mu \cdot dUt(Y1)/dZ$$

are calculated.

The vector values τ (X1, Y1) in all local coordinate systems form the wall shear stress vector. Therefore, on an area element in contact with the wall surface, the wall shear stress vector has the x and the y components defined by the x and the y directions of the area element.

Figure 23:
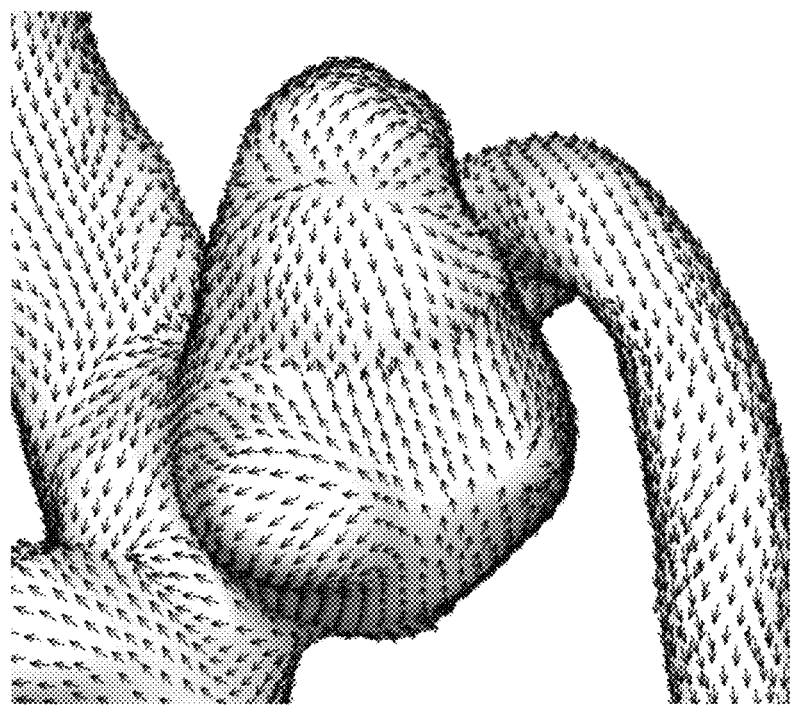
FIG. 23 shows a graphical representation of superposition of shear stress vectors on the three-dimensional shape of blood vessels.

FIG. 23 illustrates the shear stress vectors along the vascular wall by using the method described above and attached to a three-dimensional shape model.

Figure 24:
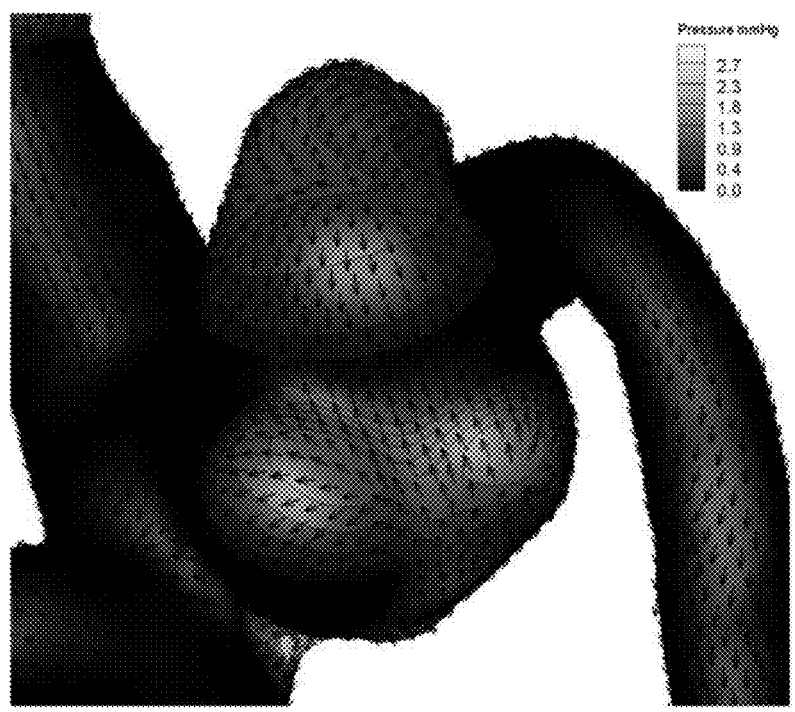
FIG. 24 shows a graphical representation of the shear stress vectors and the pressure which are superposed on the three-dimensional shape of blood vessels.

It should be noted that there is force exerting on the vascular wall in the tangential direction, and there is also the pressure P in the direction of collision against the wall. The pressure at the point G in the global coordinate system will be in the Z1 direction of the local coordinate system after the coordinate transformation. FIG. 24 superposes the colorized pressure values on FIG. 23. Area with lighter color indicates higher pressure.

The wall shear stress 71 and its vector 72 obtained for each polygon in this manner are stored in the simulation result DB 16.

(Flow Disturbance Index Calculation Unit)

Next, the flow disturbance index calculation unit 31 obtains the flow disturbance index by calculating the index numerically from the morphology of the wall shear stress vectors. The flow disturbance index is a numerical index that indicates the degree of alignment of the wall shear stress vector at a mesh with the surrounding wall shear stress vectors. In other words, the flow disturbance index is obtained by calculating each angle θ between the wall shear stress vector of a mesh targeted for obtaining the flow disturbance index (the "targeted mesh", hereinafter) and the wall shear stress vector of another mesh adjacent to the targeted mesh.

Figure 25:
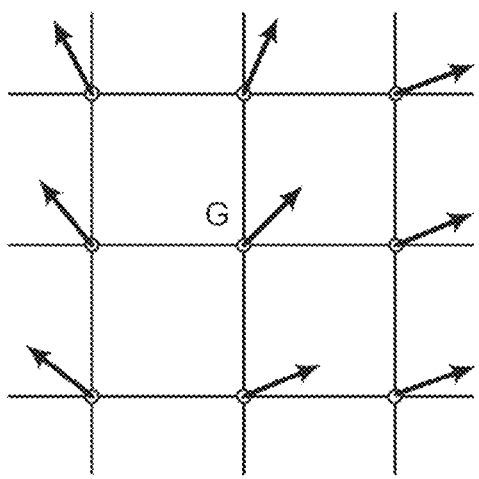
FIG. 25 explains the calculation of the flow disturbance index.

FIG. 25 illustrates an example of the relationship among the shear stress vector at an area element G (which is shown as a point for illustrative purpose) and the shear stress vectors at surrounding eight area elements. In this example, the magnitudes of the shear stress vectors are not relevant but the directions, and hence they are expressed as unit vectors to extract the directions only. Although, strictly speaking, the area elements form a three-dimensional configuration, adjacent elements are very close and hence may be treated as a two-dimensional configuration. In other words, each wall shear stress vector is projected onto a two-dimensional plane for processing. FIG. 25 illustrates a mapping of the area element G and its surrounding area elements onto the two-dimensional coordinate system.

In the embodiment of the present invention, the divergence ("div", hereinafter) and the rotation ("rot", hereinafter) operations of the vector analysis are calculated for a targeted mesh in order to obtain numerical values of the morphology of wall shear stress vectors.

That is, the components of the vector field τ (i.e., the shear stress vector) of a mesh in a three-dimensional space may be expressed as the components at a point G(x, y) which is mapped into the two-dimensional orthogonal coordinate system (x, y), which is given by the following equation.

$$\tau(G)=(\tau x(x,y),\tau y(x,y))$$

Whence the "scalar field div τ", which is called the "divergence of the vector field τ" is defined by the following equation:

$$\text{div}\,\tau = \partial \tau x/\partial x + \partial \tau y/\partial y$$

Similarly, the "scalar field rot τ", which is called the "rotation of the vector field τ" is defined by the following equation:

$$\text{rot}\,\tau = \partial \tau y/\partial x - \partial \tau x/\partial y$$

Figure 26:
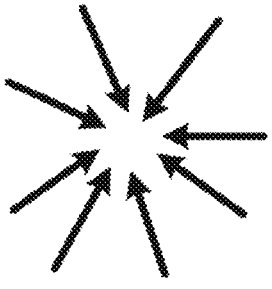
FIG. 26 shows a diagram for interpreting the flow disturbance index.

FIG. 26 depicts the relationship between the morphology of the wall shear stress vectors and the values of the aforementioned "divergence (div)" and "rotation (rot)." The morphology of the wall shear stress vectors has four categories: 1) parallel, 2) confluent, 3) rotational, and 4) divergent.

For the parallel, (div, rot)=(0, 0), for the confluent, (div, rot)=(negative value, 0), for the rotational, (div, rot)=(0, positive or negative value), for the divergent, (div, rot)= (positive value, 0). The degree of confluent and divergent types can be quantified by the div-value. That is, for the confluent type, if its negative value increases in the negative direction, the degree of confluence also increases; and for the divergent type, if its positive value increases in the positive direction, the degree of divergence also increase.

For the rotational type, depending on the direction of rotation, both the positive and the negative values appear but their absolute values may be a numerical parameter. If the flow disturbance index is defined by the vector quantity D=(div, rot), the magnitude may be used as the flow disturbance index, i.e., as the flow disturbance becomes smaller, the wall shear stress vector tends to align along with other shear stress vectors at surrounding meshes (becoming closer to the parallel type).

If there is a flow disturbance index, its magnitude (as compared with the threshold value) may be used to determine whether the blood flow is malignant or benign, and furthermore, comparing the numerical value of div with that of rot, the blood flow may be categorized to the confluent, the rotational, and or divergent type, which may be used to determine whether the aneurysmal wall is in a type of either atherosclerosis or wall thinning.

Figure 27:
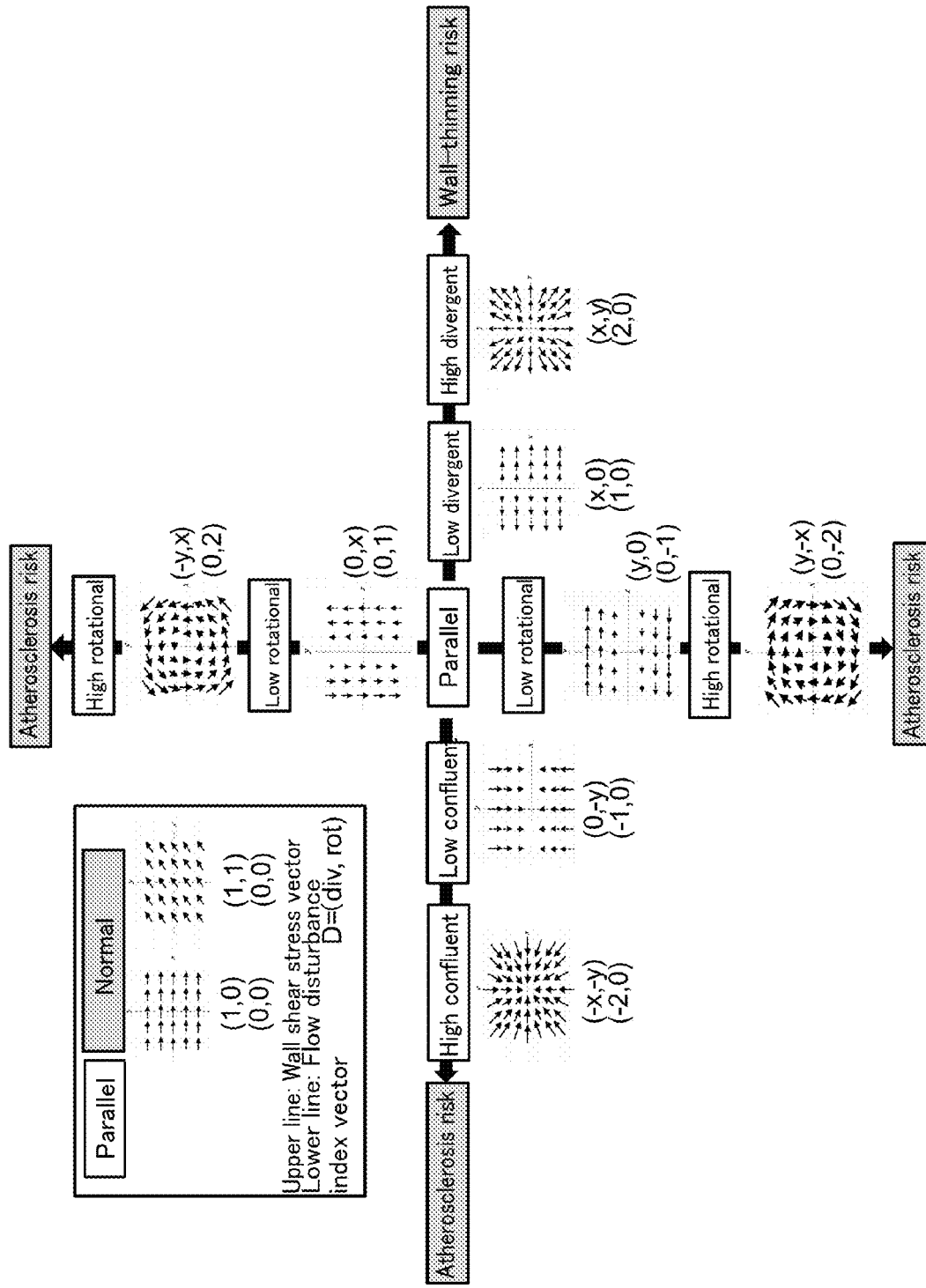
FIG. 27 shows the method for determining malignancy and benignancy with the map of flow disturbance index.

FIG. 27 shows a map of the numerical values of div and rot. Namely, this figure shows the flow disturbance index (div, rot) for a typical example of the shear stress vector. Here, the typical example is an ideal mathematical pattern but not constructed from a set of experimental data. As described above, the magnitude of the shear stress vector is converted to a unit vector having the norm one, and thus the flow disturbance index is already normalized, which makes comparison among different patients possible. In other words, the embodiment of the present invention is capable of obtaining the index that may be evaluated as the absolute value of the flow disturbance index described above.

This embodiment of the present invention may combining the flow disturbance index with the pressure on the targeted mesh as the weight coefficient to make the flow disturbance index for accurately determining the damage to the targeted blood vessel caused by the blood flow pressurizing the vascular wall. This embodiment uses the normalized pressure, i.e., the pressure index even when the pressure is used. This embodiment calculates the pressure index by each pressure divided by the mean pressure in the lump. (The calculation is a multiplication in this case).

By the above argument, in a case where, for example, the divergence type of the shear stress vectors is formed by the blood flow collision, increase of the local wall pressure may be observed from the collision of the main flow but increase of the wall pressure may not be observed from the collision of the secondary flow separated from the main flow. In such a case, combining the morphology of the shear stress vectors with pressure may refine the estimation, and in particular effectively estimate a thinning part of cerebral aneurysm. In other words, there are several methods for indexing the pressure, and hence the method for overlaying the index with the flow disturbance which is calculated from the shear stress vector may take multiplication, division, or the power law, and multiple methods are possible.

(Determination Unit)

The determination unit 32 determines if the flow at each mesh is malignant or benign according to the flow disturbance index of each mesh which is calculated by the flow disturbance index calculation unit 32. The conditions of the wall shear stress vector are: parallel to the surrounding wall stress vectors, confluent to the directions of the surrounding wall shear stress vectors, rotational along with the surrounding shear stress vectors, or divergent from the directions of the surrounding wall shear stress vectors. If the wall shear stress vector at a mesh is in the parallel condition, the blood flow characteristics at the mesh is determined to be benign whereas if the blood flow characteristics at a mesh is confluent, rotational, or divergent, the blood flow characteristics is malignant (not a benign flow) at the mesh.

Furthermore, the value of flow disturbance index in a malignant flow may be used to evaluate the degree of risk. The embodiment of the present invention estimates that the risk is higher when the value of flow disturbance index increases positively or negatively. Here the index used as the threshold value is determined in such a way that the inventors of the present invention trace the time variation of the wall shear stress vectors in a cerebral aneurysm of a patient and determine the threshold value empirically based on the correlation between the wall shear stress vectors and the actual vascular tissue of the cerebral aneurysm sampled from the patient, but the value may be changed in some case. The threshold value may further be set stepwise and the condition of the wall shear stress vector is set in several steps in order to determine the degree of the benign flow and/or the malignant flow.

Figure 28:
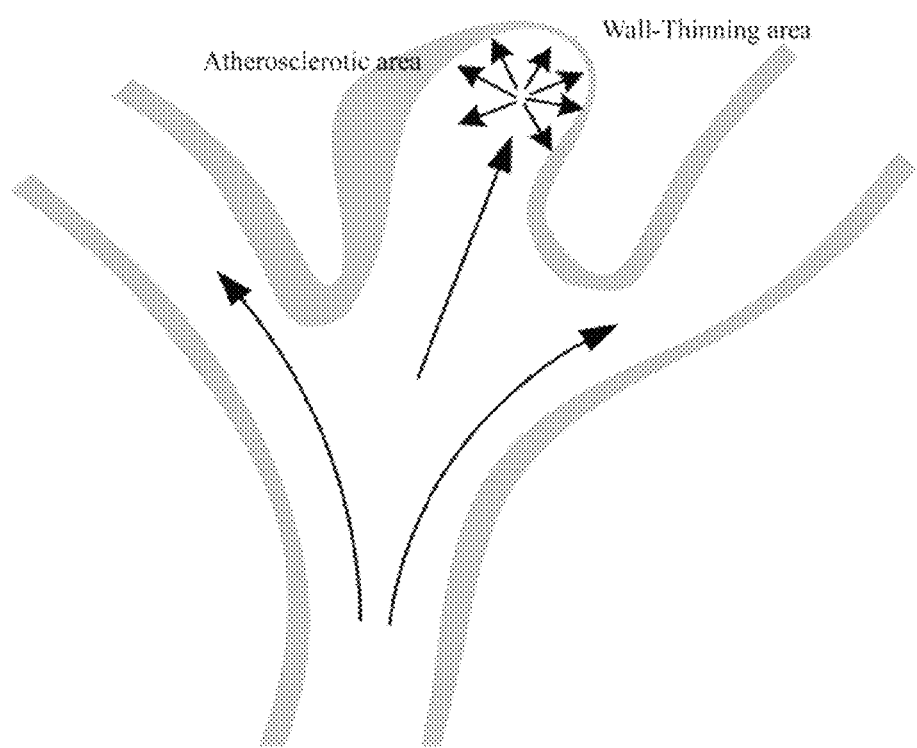
FIG. 28 illustrates the method for determining wall thinning with the flow disturbance index.

As disclosed above, the embodiment of the present invention may categorize the condition of the vascular wall thickness (i.e., the lesion tendency) according to the state of the wall shear stress vector. If the wall shear stress vector is parallel, the wall thickness is at a normal level. If the wall shear stress vector is confluent or rotational, there is a tendency where blood cells and protein in blood plasma are easily deposited, and the blood vessel turns to be an atherosclerosis type and increases the wall thickness. Furthermore, if the wall shear stress vector is divergent, it is a wall thinning type where damage and reproduction fault of endothelial cells cause a tendency in which blood cells infiltrate, proliferate, and migrate into the blood vessel, degrading the mechanical strength of the vascular wall, and as a result, decreasing the wall thickness around the lesion. FIG. 28 is a schematic diagram that shows the concept of the atherosclerosis-type and wall-thinning-type lesion.

Figure 29:
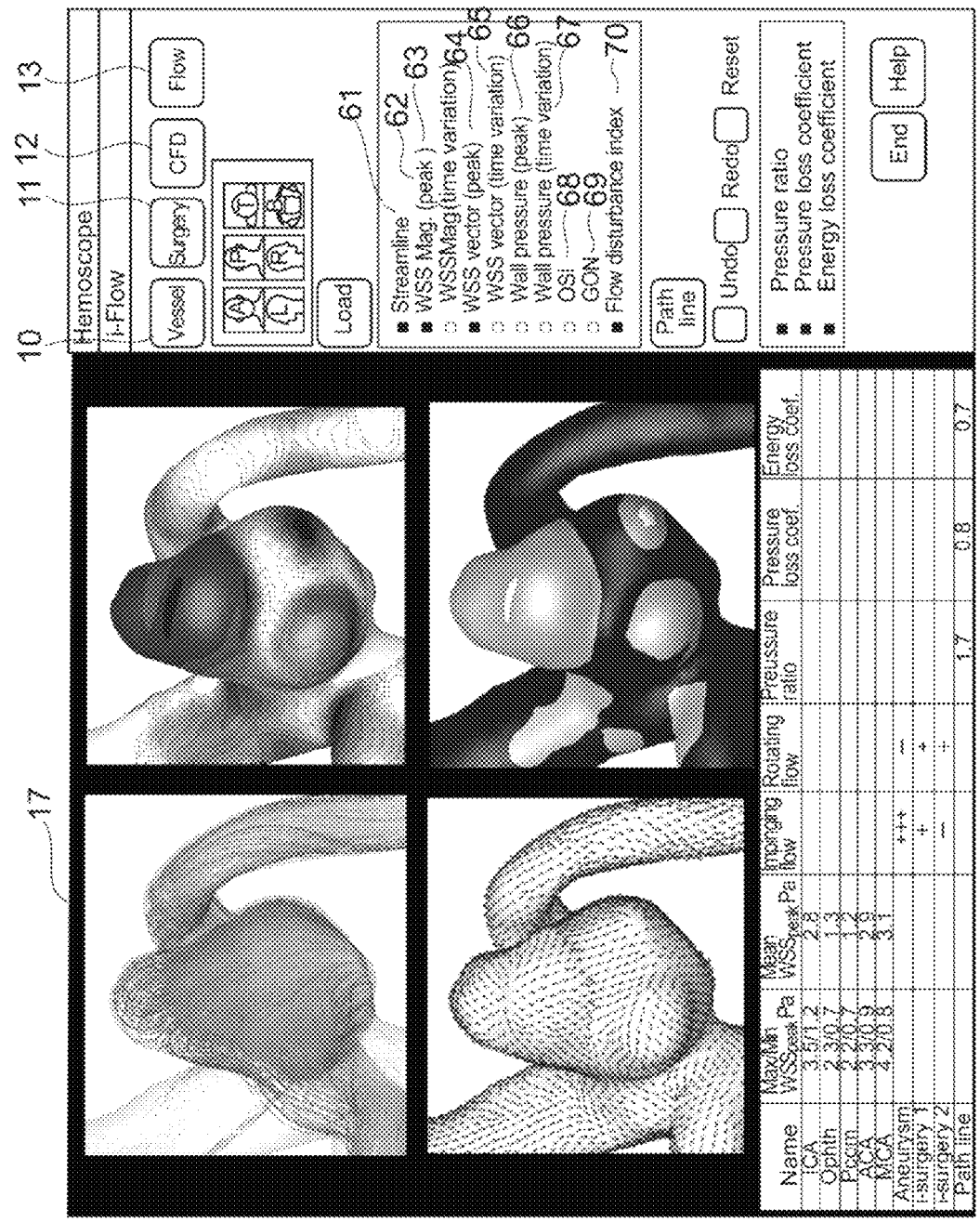
FIG. 29 depicts the graphical user interface of the blood flow characteristics determination unit.

FIG. 29 shows the user graphic interface 17 that displays the result of the blood flow characteristics determination unit 13 (the vector operation unit 30, the index calculation unit 31, and the determination unit 32). As described previously, a user pushes the <Load> button of the interface 17 to read the analytical data as the input. The user then selects the items to be displayed, from <Streamline> 61 to <Flow disturbance index> 70 to complete the display layout of the interface. The user also may select parameters of blood vessel resistance: <Pressure ratio>, <Pressure loss coefficient>, and <Energy loss>. For displaying the parameters, the user determines the starting and the ending points for the central line of the blood vessel, and then the system automatically sets the volume of test and executes various calculations. As a result, the user interface 17 displays the result of the determination.

FIGS. 30A to D enlarge an example of determination. Referring to these figures, the effectiveness and the superiority of the <Flow disturbance index> are explained hereinafter.

Figure 30A:
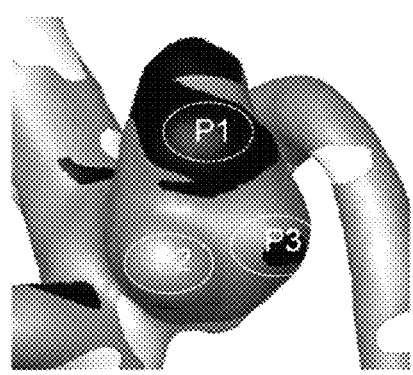
FIGS. 30A to 30D show the displayed result of the effectiveness of the flow disturbance index on determining the aneurysm wall thinning process.
Figure 30B:
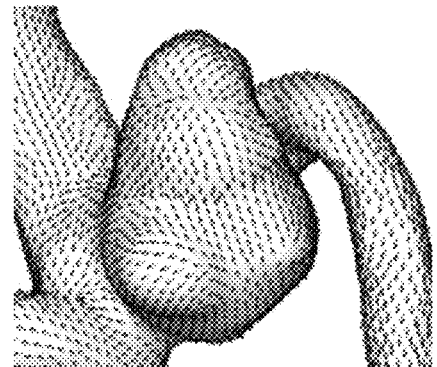
Figure 30C:
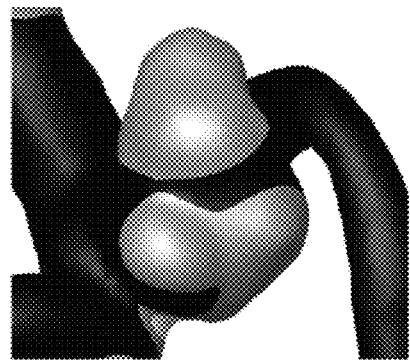
Figure 30D:
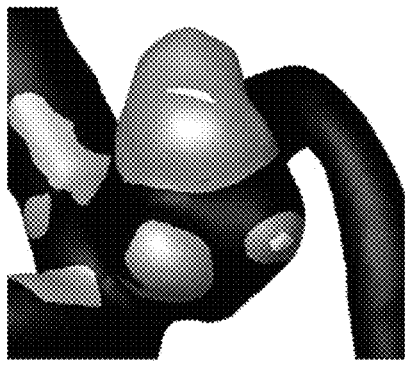

The system displays the wall shear stress, the pressure, and the flow disturbance index, each of which is normalized with the corresponding maximum value on the aneurysm wall. On the display, a thinner color indicates a larger value while a thicker color means a smaller value. For illustrative purpose, the wall shear stress (FIG. 30A) has three wall-thinning parts (P1, 2, and 3) which are identified by observing the aneurysmal wall during a surgery and analyzing the wall thickness. Because at the part P1, the wall shear stress is low while at the part P2 it is high, there is no common characteristics over the three wall-thinning parts. On the other hand, the wall shear stress vector (FIG. 30B) visualizes that the wall shear stress vectors are in the tendency of "divergent" at the 3 locations. In addition, at the locations, FIG. 30C indicates that the pressure is also high. This means that the blood flow impinges with the aneurysm wall. Calculation of the flow disturbance index (divergent) reveals particularly higher values of the flow disturbance index (divergent) at the three locations of thinner walls as shown in FIG. 30D. In this example, the location in black has the flow disturbance index 0 (parallel, i.e., a benign flow), the location in grey has the flow disturbance index 1 (divergent, i.e., a malignant flow), and the location in white has the flow disturbance index 2 (divergent, i.e., a malignant flow).

In other words, there is a correlation between the thinner part and the flow disturbance index (divergent), and it is possible to determine the thinning part of an aneurysmal wall of a patient by applying the determination of the flow disturbance index (divergent) prior to surgery.

As disclosed above, the determination unit of this system is capable of determining whether the blood flow characteristics at each mesh is malignant or benign based on the flow disturbance index, and the user interface may visualize the result. In addition to the determination result, the blood flow characteristics (including the streamline, the fluid velocity, and the pressure) at each mesh obtained by the fluid analysis unit is also displayed visually. The type and mode of displayed data is not particularly limited, and, for example, it is possible to visually recognize a region of high malignant flow density and other regions in a patient's cerebral aneurysm by colorizing begin and malignant flows at each mesh on the surface of a three-dimensional image of the cerebral aneurysm produced from three-dimensional image data of the cerebral aneurysm that are produced by the vascular shape extraction device.

The flow disturbance index and the determination result of blood flow characteristics are stored in the simulation DB 16, as the items 74 and 75 in FIG. 1. The result of determination is preferably stored so that the position (and the value) of a malignant flow is related to the value of the flow disturbance index.

In the flow disturbance index calculation unit 31, the time dependence of the flow disturbance index at each mesh may be also obtained as the flow disturbance index. That is, after calculating the flow disturbance index, the dynamical change of the flow disturbance index is calculated by using the time average of the flow disturbance index and its variation, or the time-series data, the derivative, or the frequency evaluation by using the Fourier transform. In this case, the characteristics determination means compares the calculated time change with the pre-determined threshold vale to determine if the flow is benign or malignant. In other words, if the time variation is smaller than the pre-determined threshold value, the blood flow at a mesh is benign, and on the other hand, if the time variation is larger than the pre-determined threshold value, the blood flow at the mesh is malignant. The threshold value is empirically determined based on the frequency of the heart pulsatile rate. The reason for this criterion refers to researches which discover that the shear stress on the vascular wall of cerebral aneurysm destroys vascular endothelial cells if the stress exerts at a frequency higher than the heart pulsatile rate.

The embodiment of the present invention discloses a system that determines the probability of rupture of cerebral aneurysms; however, the present invention is not limited to the aneurysm but also can be applied for other diseases in terms of determining the possible appearance of lesion in other blood vessels and its potential growth.

Furthermore, the vector operation unit may be configured as a single mathematical operation instrument that has the required functions. The mathematical operation instrument acquires the blood flow and the pressure at each unit area of the target vascular site, and calculates the wall shear stress vector on unit area of the vascular wall to produce output data of the wall shear stress vector, which may be displayed through the interface 17.

(Application to a Surgery Skill Evaluation System)

The surgical simulation described by the embodiment of the present invention may also be applied to the following surgical skill evaluation system.

For example, a user who conducted a vascular anastomosis operation using a blood vessel simulation model may process the DICOM format data of the blood vessel simulation model on which vascular anastomosis is operated by uploading the data to the sever 3 of this system. The upload routine may be also performed by applying another means such as the e-mail communication.

In this case, the blood flow analysis for a vascular anastomosis model is carried out but at the same time, it is preferable for a user itself to edit the morphology of the anastomotic part in order to conduct a simulation to investigate the procedure of vascular anastomosis or the loss of energy due to the surgery for validating the surgical technique. Therefore, in this case, in addition to the configuration of the embodiment, the system needs to have a unit for calculating the energy loss.

Figure 31:
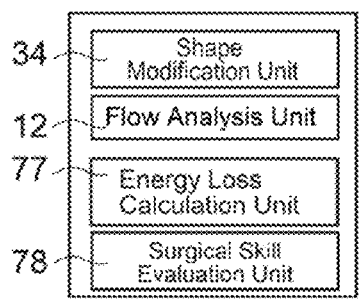
FIG. 31 shows a schematic diagram of a surgical skill evaluation system of another embodiment of the present invention.

For this purpose, as shown in FIG. 31, in addition to the fluid analysis unit 12, the program storage unit of this system has an energy loss calculation unit 77, vascular shape modification unit 36, and a surgical skill evaluation unit 78.

The energy loss calculation unit computes the energy of the blood flow at the inlet and the outlet of the model under investigation and the energy loss by using the state quantities that the fluid analysis unit calculated. The energy loss is then converted to the anastomotic stenosis rate (or the degree of stenosis) by normalizing it for the cross-section and the length of the blood vessel. The vascular shape modification unit 36 uses the configuration of the shape modification unit 36 in order to check which part of the internal shape of the anastomotic part needs to be altered for obtaining more effect on the blood flow score. The surgical skill evaluation unit 78 conducts the following evaluations based on the energy loss (or the anastomotic stenosis rate (the degree of stenosis)).

For evaluating the surgical skill during a course of training the vascular anastomosis operation, re-establishing a smooth blood flow is important. "Smooth" means there is no morphological existence of stenosis portion in the anastomotic lumen. A stenosis portion in the anastomotic lumen causes loss of energy. Hence in training the vascular anastomosis operation, it is ideal to perform anastomosis without stenosis in the anastomotic lumen. In training the vascular anastomosis operation, the stenosis is considered to be a lesion claimed above. That is, unexperienced surgical skill causes the stenosis in the anastomotic lumen, bringing a circumstance where the post-surgical blood flow has large energy loss.

The surgical simulation program possibly evaluates how to improve the stenosis by interpreting it as a lesion in the aforementioned embodiment of the present invention. For example, a user may arbitrarily edit the morphology of lesion, i.e., the morphology of stenosis (by using the vascular shape editorial functions including enlargement, reduction, and deletion) to investigate the cause and effect between the blood flow and the surgical operation. Therefore, in this example, the evaluation unit is configured to use an interface similar to the aforementioned embodiment to show the relationships between the surgical skill and the lumen morphology, and the lumen morphology and the blood flow promptly and intuitively on a computer display.

A vascular anastomosis operation using an automatic anatomic instrument and conventional suture consequently produces different anastomosis lumen. For example, an automatic anatomic instrument makes a T-shaped anatomic junction, and the anatomic cross-section is close to a circle. Thus, by enlarging or reducing the diameter of the anatomic cross-section, it is possible to simulate the result of an anastomosis operation.

It would be expected that by editing the anatomic lumen, a simulation of removing part that does not affect the post-surgical blood flow may be conducted to design a new anatomic operation and a new clinical discovery.

In addition, the configuration of the present invention is not limited to the examples depicted by the figures herein, and various modifications may be attainable within the scope of the present invention.

What is claimed is:

1. A computer-based system for determining patient-specific vascular information, the system comprising at least one computer configured to:
   store template data containing names of a principal vascular element and other vascular elements in a vascular portion of a patient, which defines relative positional relationships among the principal vascular element and the other vascular elements;
   receive first three dimensional data representing a shape of the vascular portion of the patient, the three dimensional data being suitable for simulations using computational fluid dynamics (CFD);
   determine, from the first three dimensional data, a cross-sectional area of each of vascular elements in the vascular portion of the patient, and identify a vascular element with a largest median value of the area as the principal vascular element; and
   label names to the vascular elements in the first three dimensional data, by applying the template data, based on the relative positional relationships with the principal vascular element.

2. The system of claim 1, wherein,
   the template data includes a set of mesh detail levels, each mesh detail level being associated with a respective name of a vascular element,
   the at least one computer is further configured to:
   conduct a CFD simulation using the first three dimensional data by varying the mesh detail levels according to each vascular element based on the labeled name of the vascular element.

3. The system of claim 2, the system being further configured to:
   receive an input from a user including a choice from a plurality of surgical treatments for a target site on the vascular portion, each of the surgical treatments being associated with a set of instructions to modify the first three dimensional data for the surgical treatment,
   modify the first three dimensional data according to the instructions associated with the surgical treatment chosen by the user, thereby outputting second three dimensional data representing a shape of the vascular portion of the patient in a state after said surgical treatment chosen by the user is applied to the target site, and
   receive and display, for planning a suitable surgical treatment for the patient, a result of a computational fluid dynamics (CFD) simulation on the second three dimensional data by varying the mesh detail levels according to each vascular element based on the labeled name of the vascular element.

4. The system of claim 3, the computer system being further configured to:
display the first three dimensional data, and
receive an input from the user, on the displayed first dimensional data, to specify the target site on the vascular portion.

5. The system of claim 3, the computer system being further configured to:
receive a result of a CFD simulation on the first three dimensional data, and
display the results of the CFD simulations performed on the first and second three dimensional data in a manner that enables comparisons.

6. The system of claim 3, wherein
said surgical treatments include coil embolization, and
the set of instructions to modify the first three dimensional data for coil embolization comprises an instruction to place a porous structure on a part of the three-dimensional data at the target site on the vascular portion.

7. The system of claim 6, the computer system being further configured to adjust a coil filling ratio with an aperture ratio of the porous structure.

8. The system of claim 3, wherein,
the surgical treatments include clipping,
the set of instructions to modify the first three dimensional data for clipping comprises an instruction to remove one or more polygons which constitute a surface of a part of the first three dimensional data at the target site on the vascular portion, and an instruction to regenerate the removed surface with one or more different polygons for simulating a state of blocking the part of the three dimensional data.

9. The system of claim 3, wherein,
the surgical treatments include stent implantation,
the set of instructions to modify the first three dimensional data for stent implantation comprises an instruction to modify an uneven surface on a part of the target site on the vascular portion by moving or distorting one or more polygons which configure the uneven surface in the first three dimensional data for simulating a state of controlling blood flow by the implantation of a stent.

10. The system of claim 3, wherein,
the surgical treatments include flow-diverting stent implantation,
the set of instructions to modify the first three dimensional data for the flow-diverting stent implantation comprising an instruction for defining a lattice structured object on a part of the target site on the vascular portion for simulating a restricted blood flow by implanting a flow-diverting stent.

11. The system of claim 10, wherein,
the set of instructions to modify the first three dimensional data for the flow-diverting stent implantation further comprises an instruction for adjusting a pore density with an aperture ratio of the lattice structured object.

12. The system of claim 3, wherein the result of the CFD simulation includes information relating an energy loss of blood flow at the vascular portion.

13. The system of claim 2, wherein
the result of the CFD simulation includes information relating to vascular wall vulnerability characteristics at each computational mesh on an inner surface of the vascular portion of the patient.

14. The system of claim 13, wherein,
the information relating to the vascular wall vulnerability characteristics includes a disturbance in blood flow at and around each computational mesh on the inner surface of the vascular portion of the patient.

15. The system of claim 14, the computer being further configured to
determine a disturbance based on at least a relative relationship among directions of wall shear stress vectors at and around each computational mesh on the inner surface of the vascular portion of the patient.

16. The system of claim 15, the computer being further configured to:
determine if the relative relationship among the directions of the shear stress vectors at and around each computational mesh on the inner surface of the vascular portion of the patient is "parallel", "confluent", "rotational", or "divergent", and
determine the information relating to the vascular wall vulnerability characteristics to be benign (or non-malignant) if the relative relationship is "parallel", otherwise malignant (or non-benign), and
display distinguishable symbols, each representing benign or malignant respectively, the symbols being graphically superposed on the three dimensional data.

17. A method for determining patient-specific vascular information, the method comprising the steps of:
storing template data containing names of a principal vascular element and other vascular elements in a vascular portion of a patient, which defines relative positional relationships among the principal vascular element and the other vascular elements;
receiving first three dimensional data representing a shape of the vascular portion of the patient, the three dimensional data being suitable for simulations using computational fluid dynamics (CFD);
determining, from the first three dimensional data, a cross-sectional area of each of vascular elements in the vascular portion of the patient, and identify a vascular element with a largest median value of the area as the principal vascular element; and
labeling names to the vascular elements in the first three dimensional data, by applying the template data, based on the relative positional relationships with the principal vascular element.

18. The method of claim 17, wherein,
the template data includes a set of mesh detail levels, each mesh detail level being associated with a respective name of a vascular element,
the method further comprises the step of
conducting a CFD simulation using the first three dimensional data by varying the mesh detail levels according to each vascular element based on the labeled name of the vascular element.

19. The method of claim 18, further comprising the steps of:
receiving an input from a user including a choice from a plurality of surgical treatments for a target site on the vascular portion, each of the surgical treatments being associated with a set of instructions to modify the first three dimensional data for the surgical treatment,
modifying the first three dimensional data according to the instructions associated with the surgical treatment chosen by the user, thereby outputting second three dimensional data representing a shape of the vascular portion of the patient in a state after said surgical treatment chosen by the user is applied to the target site, and receiving and displaying, for planning a suitable surgical treatment for the patient, a result of a computational fluid dynamics (CFD) simulation on the second three dimensional data by varying the mesh detail levels according to each vascular element based on the labeled name of the vascular element.

20. The method of claim 19, further comprising the steps of:
displaying the first three dimensional data, and
receiving an input from the user, on the displayed first dimensional data, to specify the target site on the vascular portion.

21. The method of claim 19, further comprising the steps of:
receiving a result of a CFD simulation on the first three dimensional data, and
displaying the results of the CFD simulations performed on the first and second three dimensional data in a manner that enables comparisons.

22. The method of claim 19, wherein
said surgical treatments include coil embolization, and
the set of instructions to modify the first three dimensional data for coil embolization comprises an instruction to place a porous structure on a part of the three-dimensional data at the target site on the vascular portion.

23. The method of claim 22, further comprising the step of adjusting a coil filling ratio with an aperture ratio of the porous structure.

24. The method of claim 19, wherein,
the surgical treatments include clipping,
the set of instructions to modify the first three dimensional data for clipping comprises an instruction to remove one or more polygons which constitute a surface of a part of the first three dimensional data at the target site on the vascular portion, and an instruction to regenerate the removed surface with one or more different polygons for simulating a state of blocking the part of the three dimensional data.

25. The method of claim 19, wherein,
the surgical treatments include stent implantation,
the set of instructions to modify the first three dimensional data for stent implantation comprises an instruction to modify an uneven surface on a part of the target site on the vascular portion by moving or distorting one or more polygons which configure the uneven surface in the first three dimensional data for simulating a state of controlling blood flow by the implantation of a stent.

26. The method of claim 19, wherein,
the surgical treatments include flow-diverting stent implantation,
the set of instructions to modify the first three dimensional data for the flow-diverting stent implantation comprising an instruction for defining a lattice structured object on a part of the target site on the vascular portion for simulating a restricted blood flow by implanting a flow-diverting stent.

27. The method of claim 26, wherein,
the set of instructions to modify the first three dimensional data for the flow-diverting stent implantation further comprises an instruction for adjusting a pore density with an aperture ratio of the lattice structured object.

28. The method of claim 19, wherein the result of the CFD simulation includes information relating an energy loss of blood flow at the vascular portion.

29. The method of claim 18, wherein
the result of the CFD simulation includes information relating to vascular wall vulnerability characteristics at each computational mesh on an inner surface of the vascular portion of the patient.

30. The method of claim 29, wherein,
the information relating to the vascular wall vulnerability characteristics includes a disturbance in blood flow at and around each computational mesh on the inner surface of the vascular portion of the patient.

31. The method of claim 30, further comprising the step of
determining a disturbance based on at least a relative relationship among directions of wall shear stress vectors at and around each computational mesh on the inner surface of the vascular portion of the patient.

32. The method of claim 31, further comprising the steps of:
determining if the relative relationship among the directions of the shear stress vectors at and around each computational mesh on the inner surface of the vascular portion of the patient is "parallel", "confluent", "rotational", or "divergent", and
determining the information relating to the vascular wall vulnerability characteristics to be benign (or non-malignant) if the relative relationship is "parallel", otherwise malignant (or non-benign), and
displaying distinguishable symbols, each representing benign or malignant respectively, the symbols being graphically superposed on the three dimensional data.

* * * * *